US010172915B2

(12) United States Patent
Zhang et al.

(10) Patent No.: US 10,172,915 B2
(45) Date of Patent: Jan. 8, 2019

(54) METHODS AND COMPOSITIONS FOR ACTIVATION OF SIRTUINS WITH ANNEXIN A1 PEPTIDES

(71) Applicant: Duke University, Durham, NC (US)

(72) Inventors: Zhiquan Zhang, Durham, NC (US); Mihai V. Podgoreanu, Chapel Hill, NC (US); Qing Ma, Durham, NC (US); David S. Warner, Chapel Hill, NC (US); Mark F. Newman, Durham, NC (US)

(73) Assignee: Duke University, Durham, NC (US)

( * ) Notice: Subject to any disclaimer, the term of this patent is extended or adjusted under 35 U.S.C. 154(b) by 125 days.

(21) Appl. No.: 14/519,000

(22) Filed: Oct. 20, 2014

(65) Prior Publication Data
US 2015/0111830 A1 Apr. 23, 2015

Related U.S. Application Data

(60) Provisional application No. 61/893,269, filed on Oct. 20, 2013.

(51) Int. Cl.
A61K 38/06 (2006.01)
A61K 38/00 (2006.01)
A61K 38/17 (2006.01)

(52) U.S. Cl.
CPC .................. A61K 38/1709 (2013.01)

(58) Field of Classification Search
None
See application file for complete search history.

(56) References Cited

U.S. PATENT DOCUMENTS

| | | | |
|---|---|---|---|
| 5,849,502 A | 12/1998 | Tsao | |
| 6,576,660 B1 * | 6/2003 | Liao | A61K 31/00 514/337 |
| 9,173,918 B2 * | 11/2015 | Zhang | A61K 38/1709 |
| 2003/0171297 A1 | 9/2003 | Perritti et al. | |
| 2006/0024315 A1 | 2/2006 | Schnitzer et al. | |
| 2007/0124086 A1 | 5/2007 | Mendrick et al. | |
| 2010/0203512 A1 | 8/2010 | Chen et al. | |
| 2010/0291053 A1 * | 11/2010 | Clayton | A61K 31/01 424/93.51 |
| 2011/0110913 A1 | 5/2011 | Grant et al. | |
| 2011/0113498 A1 | 5/2011 | Westphal et al. | |
| 2011/0124637 A1 | 5/2011 | Vu et al. | |
| 2011/0251104 A1 | 10/2011 | Ozbal et al. | |
| 2011/0257174 A1 | 10/2011 | Oalmann et al. | |
| 2011/0263564 A1 | 10/2011 | Narayan et al. | |
| 2011/0306609 A1 | 12/2011 | Oalmann et al. | |
| 2011/0318284 A1 | 12/2011 | Dal Farra et al. | |
| 2011/0319317 A1 | 12/2011 | Collard et al. | |
| 2011/0319411 A1 | 12/2011 | Vu et al. | |
| 2012/0004175 A1 | 1/2012 | Zhang et al. | |
| 2012/0022254 A1 | 1/2012 | Nunes et al. | |
| 2012/0029065 A1 | 2/2012 | Sinclair et al. | |
| 2012/0108585 A1 | 5/2012 | Vu | |
| 2012/0270790 A1 | 10/2012 | Podgoreanu et al. | |

FOREIGN PATENT DOCUMENTS

| | | | |
|---|---|---|---|
| EP | 2 361 618 A2 | 8/2011 | |
| EP | 2 362 226 A1 | 8/2011 | |
| EP | 2 388 263 A1 | 11/2011 | |
| WO | WO 2008/121881 A2 | 10/2008 | |
| WO | WO 2008121881 A2 * | 10/2008 | ........... A61K 31/404 |
| WO | WO 2010/077947 A1 | 7/2010 | |
| WO | WO 2010/101949 A1 | 9/2010 | |
| WO | WO 2011/059839 A1 | 5/2011 | |
| WO | WO 2011/116176 A1 | 9/2011 | |
| WO | WO 2011/130400 A1 | 10/2011 | |
| WO | WO 2011/130595 A2 | 10/2011 | |
| WO | WO 2011/146636 A2 | 11/2011 | |
| WO | WO 2012/001245 A1 | 1/2012 | |
| WO | WO 2012/006391 A2 | 1/2012 | |
| WO | WO 2012/024189 A2 | 2/2012 | |
| WO | WO 2012051556 A1 * | 4/2012 | ......... A61K 38/1709 |

OTHER PUBLICATIONS

Shoskes, D.A. (1998). Transplantation. 66(2):147-152; (Abstract only).*
Accession No. P04083 "ANXA1_HUMAN" (5 pages) (Nov. 26, 2014).
Accession No. P53685 "HST1_YEAST" (4 pages) (Apr. 13, 2016).
Araujo et al. "Interaction of the Anti-Inflammatory Annexin A1 Protein and Tacrolimus Immunosuppressant in the Renal Function of Rats" *American Journal of Nephrology* 31:527-533 (2010).
Araujo et al. "Annexin A1 protein attenuates cyclosporine-induced renal hemodynamics changes and macrophage infiltration in rats" *Inflammation Research* 61:189-196 (2012).
Aravindan et al. "Fenoldopam Inhibits Nuclear Translocation of Nuclear Factor Kappa Bi n a Rat Model of Surgical Ischemic Acute Renal Failure" *Journal of Cardiothoracic and Vascular Anesthesia* 20(2):179-186 (2006).
Augoustides et al. "Major Clinical Outcomes in Adults Undergoing Thoracic Aortic Surgery Requiring Deep Hypothermic Circulatory Arrest: Quantification of Organ-Based Perioperative Outcome and Detection of Opportunities for Perioperative Intervention" *Journal of Cardiothoracic and Vascular Anesthesia* 19(4):446-452 (2005).
Baur et al. "Are sirtuins viable targets for improving healthspan and lifespan?" *Nature Reviews Drug Discovery* 11:443-461 (2012).
Bell et al. "The SirT3 Divining Rod Points to Oxidative Stress" *Molecular Cell* 42:561-568.
Bellomo et al. "Acute renal failure—definition, outcome measures, animal models, fluid therapy and information technology needs: the Second International Consensus Conference of the Acute Dialysis Quality Initiative (ADQI) Group" *Critical Care* 8:R204-R212 (2004).
Berendsen, Herman J. C. "A Glimpse of the Holy Grail?" *Science* 282:642-643 (1998).

(Continued)

*Primary Examiner* — Christine J Saoud
*Assistant Examiner* — Jon M Lockard
(74) *Attorney, Agent, or Firm* — Myers Bigel, P.A.

(57) ABSTRACT

The present invention provides a method of treating, ameliorating or inhibiting sirtuin-associated disorders and/or conditions in a subject in need thereof, by administering to the subject an effective amount of an ANXA1 peptide.

2 Claims, 19 Drawing Sheets
Specification includes a Sequence Listing.

(56) References Cited

OTHER PUBLICATIONS

Bizzarro et al. "Annexin A1 N-Terminal Derived Peptide Ac2-26 Stimulates Fibroblast Migration in High Glucose Conditions" *PLoS ONE* 7(9):e45639 (2012).
Bradley et al. "Limits of Cooperativity in a Structurally Modular Protein: Response of the Notch Ankyrin Domain to Analogous Alanine Substitutions in Each Repeat" *Journal of Molecular Biology* 324:373-386 (2002).
Brenmoehl et al. "Dual control of mitochondrial biogenesis by sirtuin 1 and sirtuin 3" *Mitochondrion* 13(6):755-761 (2013).
Cao et al. "In vivo transfection of NF-kB decoy oligodeoxynucleotides attenuate renal ischemia/reperfusion injury in rats" *Kidney International* 65:834-845 (2004).
Daemen et al. "Apoptosis and Inflammation in Renal Repefusion Injury" *Transplantation* 73(11):1693-1700 (2002).
Damazo et al. "Critical Protective Role for Annexin 1 Gene Expression in the Endotoxemic Murine Microcirculation" *American Journal of Pathology* 166(6):1607-1617 (2005).
Devarajan, Prasad "Update on Mechanisms of Ischemic Acute Kidney Injury" *Journal of the American Society of Nephrology* 17:1503-1520 (2006).
Dirksen et al. "Reperfusion injury in humans: A review of clinical trials on reperfusion irjury inhibitory strategies" *Cardiovascular Research* 74:343-355 (2007).
Ernst et al. "An Annexin 1 N-Terminal Peptide Activates Leukocytes by Triggering Different Members of the Formyl Peptide Receptor Family" *The Journal of Immunology* 172:7669-7676 (2004).
Facto et al. "Annexin 1 mimetic peptide protects against renal ischemia/reperfusion injury in rats" *Journal of Molecular Medicine* 89:51-63 (2011).
Finley et al. "Metabolic regulation by SIRT3: implications for tumorigenesis" *Trends in Molecular Science* 18(9):516-523 (2012).
Gastardelo et al. "Functional and Ultrastructural Analysis of Annexin A1 and Its Receptor in Extravasating Neutrophils during Acute Inflammation" *The American Journal of Pathology* 174(1):177-183 (2009).
Gavins et al. "Annexin 1 and Melanocortin Peptide Therapy for Protection Against Ischaemic-Reperfusion Damage in the Heart" *The Scientific World Journal* 6:1008-1023 (2006).
Gavins et al. "Activation of the annexin 1 counter-regulatory circuit affords protection in the mouse brain microcirculation" *The FASEB Journal* 21:1751-1758 (2007).
GenBank Accession No. AAH01042 Sirtuin (silent mating type information regulation 2 homolog) 3 (S. cerevisiae) [*Homo sapiens*] (2 pages) (Jul. 15, 2006).
GenBank Accession No. AF083106 "*Homo sapiens* sirtuin type 1 (SIRT1) mRNA, complete cds" (2 pages) (Apr. 14, 2000).
GenBank Accession No. X05908.1 "*Homo sapiens* mRNA for lipocortin" *NCBI* 2 pages (Nov. 26, 2008).
Giralt et al. "SIRT3, a pivotal actor in mitochondrial functions: metabolism, cell death and aging" *Biochemical Journal* 444:1-10 (2012).
Haase et al. "Novel Biomarkers, Oxidative Stress, and the Role of Labile Iron Toxicity in Cardiopulmonary Bypass-Associated Acute Kidney Injury" *Journal of the American College of Cardiology* 55(19):2024-2033 (2010).
Hayhoe et al. "Annexin 1 and its bioactive peptide inhibit neutrophil-endothelium interactions under flow: indication of distinct receptor involvement" *Blood* 107:2123-2130 (2006).
Hoffman et al. "Receptor Up-regulation, Internalization, and Interconverting Receptor States" *The Journal of Biological Chemistry* 271(31):18394-18404 (1996).
Huang et al. "Mitochondrial sirtuins" *Biochimica et Biophysica Acta* 1804:1645-1651 (2010).
Kamal et al. "An annexin 1 (ANXA1)-derived peptide inhibits prototype antigen-driven human T cell Th1 and Th2 responses in vitro" *Clinical and Experimental Allergy* 31:1116-1125 (2001).

Kosicka-Knox et al. "Ac 2-26, an annexin A1-derived peptide, reduces inflammation in human SGBS adipocytes after hypoxia treatment" *Endocrine Abstracts* 29:P1172 (2012) (Abstract Only).
Kourliouros et al. "Low cardiopulmonary bypass perfusion temperatures are associated with acute kidney injury following coronary artery bypass surgery" *European Journal of Cardio-thoracic Surgery* 37:704-709 (2010).
La et al. "Annexin 1 peptides protect against experimental myocardial ischemia-reperfusion: analysis of their mechanism of action" *The FASEB Journal* 15:2247-2256 (2001).
Leoni et al. "Annexin A1, formyl peptide receptor, and NOX1 orchestrate epithelial repair" *The Journal of Clinical Investigation* 123(1):443-454 (2013).
Lim et al. "Annexin 1: the new face of an old molecule" *The FASEB Journal* 21:968-975 (2007).
Meldrum et al. "Intracellular Signaling Mechanisms of Sex Hormones in Acute Myocardial Inflammation and Injury" *Frontiers in Bioscience* 10:1835-1867 (2005).
Mishra et al. "Amelioration of Ischemic Acute Renal Injury by Neutrophil Gelatinase-Associated Lipocalin" *Journal of the American Society of Nephrology* 15:3073-3082 (2004).
Movitz et al. "The Annexin I Sequence $Gln^9$-$Ala^{10}$-$Trp^{11}$-$Phe^{12}$ Is a Core Structure for Interaction with the Formyl Peptide Receptor 1" *The Journal of Biological Chemistry* 285(19):14338-14345 (2010).
Murphy et al. "An initial evaluation of post-cardiopulmonary bypass acute kidney injury in swine" *European Journal of Cardio-thoracic Surgery* 36:849-855 (2009).
Ngo et al. "Computational Complexity, Protein Structure Prediction, and the Levinthal Paradox" *The Protein Folding Problem and Tertiary Structure Prediction* pp. 491-494 (1992).
NCBI Accession No. NM_012238 "*Homo sapiens* sirtuin 1 (SIRT1), transcript variant 1, mRNA" (9 pages) (Sep. 29, 2015).
NCBI Accession No. NP_001017524 "NAD-dependent protein deacetylase sirtuin-3, mitochondrial isoform b [*Homo sapiens*]" (3 pages) (Mar. 15, 2015).
NCBI Accession No. NP_036369 "NAD-dependent protein deacetylase sirtuin-2 isoform 1 [*Homo sapiens*]" (3 pages) (Mar. 15, 2015).
NCBI Accession No. NP_036370 "NAD-dependent protein deacetylase sirtuin-1 isoform a [*Homo sapiens*]" (6 pages) (Sep. 29, 2015).
NCBI Accession No. NP_036371 "NAD-dependent protein deacetylase sirtuin-3, mitochondrial isoform a [*Homo sapiens*]" (3 pages) (Mar. 15, 2015).
NCBI Accession No. NP_071878 "NAD-dependent protein deacetylase sirtuin-3 isoform 1 [Mus musculus]" (3 pages) (Feb. 15, 2015).
NCBI Accession No. NP_085096 "NAD-dependent protein deacetylase sirtuin-2 isoform 2 [*Homo sapiens*]" (3 pages) (Mar. 15, 2015).
NCBI Accession No. NP_501912 "yeast SIR related family member (sir-2.1) [Caenorhabditis elegans]" (2 pages) (Nov. 13, 2008).
Parikh et al. "Urinary IL-18 is an early predictive biomarker of acute kidney injury after cardiac surgery" *Kidney International* 70:199-203 (2006).
Patel et al. "Phosphodiesterase-5 Inhibition Prevents Postcardiopulmonary Bypass Acute Kidney Injury in Swine" *The Annals of Thoracic Surgery* 92:2168-2176 (2011).
Patel et al. "Prevention of post-cardiopulmonary bypass acute kidney injury by endothelin A receptor blockade" *Critical Care Medicine* 39:793-802 (2011).
Pelzer et al. "17β-Estradiol Prevents Programmed Cell Death in Cardiac Myocytes" *Biochemical and Biophysical Research Communications* 268:192-200 (2000).
Perretti et al. "Involvement of the Receptor for Formylated Peptides in the in Vivo Anti-Migratory Actions of Annexin 1 and its Mimetics" *American Journal of Pathology* 158(6):1969-1973 (2001).
Perretti et al. "Annexin 1: An Endogenous Anti-Inflammatory Protein" *Physiology* 18:60-64 (2003).
Pillai et al. "Mitochondrial SIRT3 and heart disease" *Cardiovascular Research* 88(2):250-258 (2010).
Pruitt et al. "Inhibition of SIRT1 Reactivates Silenced Cancer Genes without Loss of Promoter DNA Hypermethylation" *PloS Genetics* 2(3):e40 (2006).
Qing et al. "Novel Annexin A1 Tripeptide Ameliorates Acute Kidney Injury after Deep Hypothermic Circulatory Arrest" *ASA Abstracts* Abstract A092:1-2 (Oct. 16, 2010).

(56) References Cited

OTHER PUBLICATIONS

Ritchie et al. "Cardioprotective actions of an N-terminal fragment of annexin-1 in rat myocardium in vitro" *European Journal of Pharmacology* 461:171-179 (2003).
Ritchie et al. "Annexin-1 peptide Anx-1$_{2-26}$ protects adult rat cardiac myocytes from cellular injury induced by simulated ischaemia" *British Journal of Pharmacology* 145:495-502 (2005).
Rosner et al. "Acute Kidney Injury Associated with Cardiac Surgery" *Clinical Journal of the American Society of Nephrology* 1:19-32 (2006).
Rudinger, J. "Characteristics of the amino acids as components of a peptide hormone sequence" *Peptide Hormones* pp. 1-7 (1976).
Sack, Michael N. "The role of SIRT3 in mitochondrial homeostasis and cardiac adaptation to hypertrophy and aging" *Journal of Molecular and Cellular Cardiology* 52:520-525 (2012).
Sheridan et al. "Cell biology and molecular mechanisms of injury in ischemic acute renal failure" *Current Opinion in Nephrology and Hypertension* 9:427-434 (2000).
SIGMA Genosys "Designing Custom Peptides" *Technical Bulletin* 2 pages (2004).
Su et al. "Acute hyperglycemia exacerbates myocardial ischemia/reperfusion injury and blunts cardioprotective effect of GIK" *American Journal of Physiology—Endocrinology and Metabolism* 293:E629-E635 (2007).
Tanno et al. "Emerging beneficial roles of sirtuins in heart failure" *Basic Research in Cardiology* 107(273):1-14 (2012).
Valen et al. "Nuclear Factor Kappa-B and the Heart" *Journal of the American College of Cardiology* 38(2):307-314 (2001).
Voet et al. "Abnormal Hemoglobins" *Biochemistry* Section 9-3:235-241 (1995).
Yellon et al. "Myocardial Reperfusion Injury" *The New England Journal of Medicine* 357:1121-1135 (2007).
Zhai et al. "Effect of estrogen on global myocardial ischemia-reperfusion injury in female rats" *American Journal of Physiology—Heart and Circulatory Physiology* 279:H2766-H2775 (2000).
Zhang et al. "Abstract 3007: Annexin-A1 Mimetic Peptide and PPAR-alpha Agonist Attenuate Hyperglycemic Exacerbation of Myocardial Ischemia/Reperfusion Injury Following Cardioplegic Arrest in the Rat" *Circulation* 120:S731 (2009) (Abstract Only).
Zhang et al. "A Novel Annexin A1 Peptide Attenuates Perioperative Myocardial Injury Exacerbated by Hyperglycemia" *ASA Abstracts* Abstract A765:1-2 (Oct. 19, 2009).
Zhang et al. "Abstract 19839: Annexin-a1 Tripeptide is Cardioprotective in Several Preclinical Models of Ischemia-Reperfusion Through Resolution of Myocardial Inflammation" *Abstracts from Scientific Sessions* 122(21 Supplement):3 pages (2010) (Abstract Only).
Zhang et al. "Annexin 1 Induced by Anti-Inflammatory Drugs Binds to NF-kB and Inhibits Its Activation: Anticancer Effects In vitro and In vivo" *Cancer Research* 70(6):2379-2388 (2010).

\* cited by examiner

SEQUENCE LISTING

```
<160> NUMBER OF SEQ ID NOS: 10

<210> SEQ ID NO 1
<211> LENGTH: 1399
<212> TYPE: DNA
<213> ORGANISM: Homo sapiens
<220> FEATURE:
<221> NAME/KEY: CDS
<222> LOCATION: (75)..(1112)

<400> SEQUENCE: 1
agtgtgaaat cttcagagaa gaatttctct ttagttcttt gcaagaaggt agagataaag      60 acacttttc aaaa atg gca atg gta tca gaa ttc ctc aag cag gcc tgg       110
              Met Ala Met Val Ser Glu Phe Leu Lys Gln Ala Trp
                1               5                  10 ttt att gaa aat gaa gag cag gaa tat gtt caa act gtg aag tca tcc      158
Phe Ile Glu Asn Glu Glu Gln Glu Tyr Val Gln Thr Val Lys Ser Ser
        15                  20                  25 aaa ggt ggt ccc gga tca gcg gtg agc ccc tat cct acc ttc aat cca      206
Lys Gly Gly Pro Gly Ser Ala Val Ser Pro Tyr Pro Thr Phe Asn Pro
    30                  35                  40 tcc tcg gat gtc gct gcc ttg cat aag gcc ata atg gtt aaa ggt gtg      254
Ser Ser Asp Val Ala Ala Leu His Lys Ala Ile Met Val Lys Gly Val
45                  50                  55                  60 gat gaa gca acc atc att gac att cta act aag cga aac aat gca cag      302
Asp Glu Ala Thr Ile Ile Asp Ile Leu Thr Lys Arg Asn Asn Ala Gln
                65                  70                  75 cgt caa cag atc aaa gca gca tat ctc cag gaa aca gga aag ccc ctg      350
Arg Gln Gln Ile Lys Ala Ala Tyr Leu Gln Glu Thr Gly Lys Pro Leu
            80                  85                  90 gat gaa aca ctt aag aaa gcc ctt aca ggt cac ctt gag gag gtt gtt      398
Asp Glu Thr Leu Lys Lys Ala Leu Thr Gly His Leu Glu Glu Val Val
        95                  100                 105 tta gct ctg cta aaa act cca gcg caa ttt gat gct gat gaa ctt cgt      446
Leu Ala Leu Leu Lys Thr Pro Ala Gln Phe Asp Ala Asp Glu Leu Arg
    110                 115                 120 gct gcc atg aag ggc ctt gga act gat gaa gat act cta att gag att      494
Ala Ala Met Lys Gly Leu Gly Thr Asp Glu Asp Thr Leu Ile Glu Ile
125                 130                 135                 140 ttg gca tca aga act aac aaa gaa atc aga gac att aac agg gtc tac      542
Leu Ala Ser Arg Thr Asn Lys Glu Ile Arg Asp Ile Asn Arg Val Tyr
                145                 150                 155 aga gag gaa ctg aag aga gat ctg gcc aaa gac ata acc tca gac aca      590
Arg Glu Glu Leu Lys Arg Asp Leu Ala Lys Asp Ile Thr Ser Asp Thr
            160                 165                 170 tct gga gat ttt cgg aac gct ttg ctt tct ctt gct aag ggt gac cga      638
Ser Gly Asp Phe Arg Asn Ala Leu Leu Ser Leu Ala Lys Gly Asp Arg
        175                 180                 185 tct gag gac ttt ggt gtg aat gaa gac ttg gct gat tca gat gcc agg      686
Ser Glu Asp Phe Gly Val Asn Glu Asp Leu Ala Asp Ser Asp Ala Arg
    190                 195                 200 gcc ttg tat gaa gca gga gaa agg aga aag ggg aca gac gta aac gtg      734
Ala Leu Tyr Glu Ala Gly Glu Arg Arg Lys Gly Thr Asp Val Asn Val
205                 210                 215                 220 ttc aat acc atc ctt acc acc aga agc tat cca caa ctt cgc aga gtg      782
Phe Asn Thr Ile Leu Thr Thr Arg Ser Tyr Pro Gln Leu Arg Arg Val
```

| | | | | | | | | | | | | | | | | |
|---|---|---|---|---|---|---|---|---|---|---|---|---|---|---|---|---|
| | | 225 | | | | 230 | | | | | 235 | | | | | |
| ttt | cag | aaa | tac | acc | aag | tac | agt | aag | cat | gac | atg | aac | aaa | gtt | ctg | 830 |
| Phe | Gln | Lys | Tyr | Thr | Lys | Tyr | Ser | Lys | His | Asp | Met | Asn | Lys | Val | Leu | |
| | | 240 | | | | | 245 | | | | | 250 | | | | |
| gac | ctg | gag | ttg | aaa | ggt | gac | att | gag | aaa | tgc | ctc | aca | gct | atc | gtg | 878 |
| Asp | Leu | Glu | Leu | Lys | Gly | Asp | Ile | Glu | Lys | Cys | Leu | Thr | Ala | Ile | Val | |
| | | | 255 | | | | | 260 | | | | | 265 | | | |
| aag | tgc | gcc | aca | agc | aaa | cca | gct | ttc | ttt | gca | gag | aag | ctt | cat | caa | 926 |
| Lys | Cys | Ala | Thr | Ser | Lys | Pro | Ala | Phe | Phe | Ala | Glu | Lys | Leu | His | Gln | |
| 270 | | | | | 275 | | | | | 280 | | | | | | |
| gcc | atg | aaa | ggt | gtt | gga | act | cgc | cat | aag | gca | ttg | atc | agg | att | atg | 974 |
| Ala | Met | Lys | Gly | Val | Gly | Thr | Arg | His | Lys | Ala | Leu | Ile | Arg | Ile | Met | |
| 285 | | | | 290 | | | | | 295 | | | | | 300 | | |
| gtt | tcc | cgt | tct | gaa | att | gac | atg | aat | gat | atc | aaa | gca | ttc | tat | cag | 1022 |
| Val | Ser | Arg | Ser | Glu | Ile | Asp | Met | Asn | Asp | Ile | Lys | Ala | Phe | Tyr | Gln | |
| | | | 305 | | | | | 310 | | | | | 315 | | | |
| aag | atg | tat | ggt | atc | tcc | ctt | tgc | caa | gcc | atc | ctg | gat | gaa | acc | aaa | 1070 |
| Lys | Met | Tyr | Gly | Ile | Ser | Leu | Cys | Gln | Ala | Ile | Leu | Asp | Glu | Thr | Lys | |
| | | | 320 | | | | | 325 | | | | | 330 | | | |
| gga | gat | tat | gag | aaa | atc | ctg | gtg | gct | ctt | tgt | gga | gga | aac | | | 1112 |
| Gly | Asp | Tyr | Glu | Lys | Ile | Leu | Val | Ala | Leu | Cys | Gly | Gly | Asn | | | |
| | | | 335 | | | | | 340 | | | | | 345 | | | | taaacattcc cttgatggtc tcaagctatg atcagaagac tttaattata tattttcatc    1172 ctataagctt aaataggaaa gtttcttcaa caggattaca gtgtagctac ctacatgctg    1232 aaaaatatag cctttaaatc attttttatat tataactctg tataatagag ataagtccat   1292 ttttaaaaa tgttttcccc aaaccataaa accctataca agttgttcta gtaacaatac    1352 atgagaaaga tgtctatgta gctgaaaata aaatgacgtc acaagac                  1399

<210> SEQ ID NO 2
<211> LENGTH: 346
<212> TYPE: PRT
<213> ORGANISM: Homo sapiens

<400> SEQUENCE: 2

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe

```
                165                 170                 175

Arg Asn Ala Leu Leu Ser Leu Ala Lys Gly Asp Arg Ser Glu Asp Phe
        180                 185                 190

Gly Val Asn Glu Asp Leu Ala Asp Ser Asp Ala Arg Ala Leu Tyr Glu
            195                 200                 205

Ala Gly Glu Arg Arg Lys Gly Thr Asp Val Asn Val Phe Asn Thr Ile
210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 3
<211> LENGTH: 4
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

<400> SEQUENCE: 3

Lys Gln Ala Trp
1

<210> SEQ ID NO 4
<211> LENGTH: 4
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is optionally acetylated

<400> SEQUENCE: 4

Phe Gln Ala Trp
1

<210> SEQ ID NO 5
<211> LENGTH: 6
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
```

<223> OTHER INFORMATION: N-terminal is acetylated

<400> SEQUENCE: 5

Phe Leu Lys Gln Ala Trp
1               5

<210> SEQ ID NO 6
<211> LENGTH: 7
<212> TYPE: PRT
<213> ORGANISM: Artificial
<220> FEATURE:
<223> OTHER INFORMATION: Synthetic ANXA1 peptide

<400> SEQUENCE: 6

Glu Phe Leu Lys Gln Ala Trp
1               5

<210> SEQ ID NO 7
<211> LENGTH: 6
<212> TYPE: PRT
<213> ORGANISM: Artificial
<220> FEATURE:
<223> OTHER INFORMATION: Synthetic ANXA1 peptide

<400> SEQUENCE: 7

Phe Leu Lys Gln Ala Trp
1               5

<210> SEQ ID NO 8
<211> LENGTH: 11
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is optionally acetylated

<400> SEQUENCE: 8

Ala Met Val Ser Glu Phe Leu Lys Gln Ala Trp
1               5                   10

<210> SEQ ID NO 9
<211> LENGTH: 9
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

<400> SEQUENCE: 9

Val Ser Glu Phe Leu Lys Gln Ala Trp
1               5

<210> SEQ ID NO 10
<211> LENGTH: 25
<212> TYPE: PRT
<213> ORGANISM: Artificial
<220> FEATURE:
<223> OTHER INFORMATION: Synthetic ANXA1 peptide
<220> FEATURE:
<221> NAME/KEY: MISC_FEATURE
<222> LOCATION: (1)..(1)
<223> OTHER INFORMATION: N-terminal is acetylated

```
<400> SEQUENCE: 10

Ala Met Val Ser Glu Phe Leu Lys Gln Ala Trp Phe Ile Glu Asn Glu
1               5                   10                  15

Glu Gln Glu Tyr Val Gln Tyr Val Lys
            20              25
```

METHODS AND COMPOSITIONS FOR ACTIVATION OF SIRTUINS WITH ANNEXIN A1 PEPTIDES

STATEMENT OF PRIORITY

This application claims the benefit, under 35 U.S.C. § 119(e), of U.S. Application Ser. No. 61/893,269, filed Oct. 20, 2013, the entire contents of which are incorporated by reference herein.

STATEMENT OF GOVERNMENT SUPPORT

This invention was made with government support under Grant No. R01 HL092071 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5405-467_ST25.txt, 11,041 bytes in size, generated on Oct. 20, 2014 and filed via EFS-Web, is provided in lieu of a paper copy. This Sequence Listing is hereby incorporated by reference into the specification for its disclosures.

FIELD OF THE INVENTION

The present invention relates to compositions and methods for the treatment of disorders and/or conditions associated with reduced and/or aberrant sirtuin (SIRT) levels and/or activity by activating one or more than one SIRT in a subject using Annexin-A1 (ANXA1) peptides.

BACKGROUND OF THE INVENTION

Emerging evidence indicates that a crucial post-translational lysine deacetylation has been identified as an important regulator of gene expression as well as enzyme activities that are involved in various biological functions, including mitochondrial function. Sirtuins (SIRTs) are $NAD^+$-dependent protein deacetylases that mediate this post-translational modification by removing the acetyl groups from a wide range of proteins that have been demonstrated to be important in longevity pathways, DNA repair, antioxidant enzyme activity, and control of metabolic enzymes.

Seven members of the SIRT family have been identified in mammals. All share the same highly conserved $NAD^+$-binding site and a Sir2 catalytic core domain with variable amino and carboxyl residues. SIRT1-3 and SIRT5-7 catalyze $NAD^+$-dependent substrate-specific protein deacetylation, whereas SIRT4 acts as a $NAD^+$-dependent mono-ADP-ribosyltransferase. SIRT6 has both deacetylase and auto-ADP-ribosyltransferase properties.

Annexin-A1 (ANXA1), a 37 kDa protein, is a member of the annexin superfamily, which includes 13 calcium and phospholipid binding proteins with a significant degree of biological and structural homology (40-60%). ANXA1, originally identified as a mediator of the anti-inflammatory effects of glucocorticoids, has diverse biological functions including the regulation of inflammatory pathways, cell proliferation machinery, cell death signaling, and the process of carcinogenesis. Altering the expression or the localization of this protein can contribute to the pathogenesis of human diseases including inflammatory diseases, cardiovascular diseases and cancer.

It is an object of the present invention to provide new compositions comprising ANXA1 peptides, and methods of using such compositions, to treat diseases and disorders associated with reduced and/or aberrant SIRT amount and/or activity.

SUMMARY OF THE INVENTION

In one aspect, the present invention provides a method of increasing the amount and/or the activity of one or more than one sirtuin (SIRT) in a subject (e.g., a subject in need thereof), comprising administering to the subject an effective amount of an ANXA1 peptide (e.g., an ANXA1 short peptide (ANXA1sp)).

In various aspects of the methods of this invention, the subject has, is suspected of having, or is at increased risk of having a SIRT-associated disease or disorder, such as a sirtuin-associated cancer, type 2 diabetes, a metabolic disorder, obesity, a fat-related metabolic disorder, a neurodegenerative disorder, a disorder resulting in cognitive decline, a spinal cord injury, a blood coagulation disorder, an ocular disorder, a respiratory disorder, a viral infection, a fungal infection, chronic hepatitis infection, an autoimmune disorder, flushing, a mitochondrial disease or disorder, a chemotherapy-induced neuropathy, neuropathy associated with an ischemic event, cardiovascular disease, a disorder associated with aging, a disorder associated with stress, stroke, arthritis, hypertension, Alzheimer's disease, liver disease, a disorder that would benefit from increased mitochondrial activity, an inflammatory disorder, muscle tissue damage associated with hypoxia or ischemia, trauma, ischemia, chronic pain (e.g., trauma, ischemia and/or chronic pain associated with diseases, disorders and/or damage to the brain and/or spinal cord), and any combination thereof.

In a further aspect, the present invention provides a method of increasing the lifespan and/or health span of a subject, delaying cellular senescence of cells in a subject, preventing or inhibiting apoptosis of cells in a subject, mimicking the effects of caloric restriction in a subject and/or increasing resistance of cells to stress in a subject, comprising administering to the subject an amount of an ANXA1 peptide (e.g., an ANXA1 short peptide) that is effective in increasing the amount and/or activity of one or more than one SIRT in the subject, thereby increasing the lifespan and/or health span of the subject, delaying cellular senescence of cells in the subject, preventing or inhibiting apoptosis of cells in the subject, mimicking the effects of caloric restriction in the subject and/or increasing resistance of cells to stress in the subject, in any combination.

Also provided herein as a further aspect is a method of treating a skin disorder and/or inhibiting the effects of ageing on skin cells in a subject, comprising contacting the skin cells of the subject with an amount of an ANXA peptide (e.g. an ANXA1 short peptide (ANXA1sp)) that is effective in increasing the amount and/or activity of one or more than one SIRT in the skin cells, thereby treating a skin disorder and/or inhibiting the effects of ageing on skin cells in the subject.

In addition, the present invention provides a method of enhancing muscle performance and/or improving physical endurance in a subject, comprising administering to the subject an amount of an ANXA1 peptide (e.g. an ANXA1 short peptide (ANXA1sp)) effective in increasing the amount and/or activity of one or more than one SIRT in the subject, thereby enhancing muscle performance and/or improving physical endurance in the subject.

Further provided herein is a method of increasing the lifespan of a cell, comprising contacting the cell with an amount of an ANXA1 peptide (e.g., an ANXA1 short peptide (ANXA1sp)) effective in increasing the amount and/or activity of one or more than one SIRT in the cell, thereby increasing the lifespan of the cell. In some embodiments, the cell can be in a subject. In some embodiments, the subject can be a human.

An additional aspect of the invention is a kit for increasing the amount and/or activity of one or more than one SIRT in a subject in need thereof, comprising an ANXA1 peptide (e.g., ANXA1 short peptide (ANXA1sp)) and instructions for use.

Further aspects include the use of an ANXA1 peptide (e.g., an ANXA1 short peptide (ANXA1sp)) in the manufacture of a medicament for the treatment of a SIRT-associated disease and/or disorder as described herein in a subject (e.g., a subject in need thereof).

DETAILED DESCRIPTION OF THE INVENTION

Figure 1:
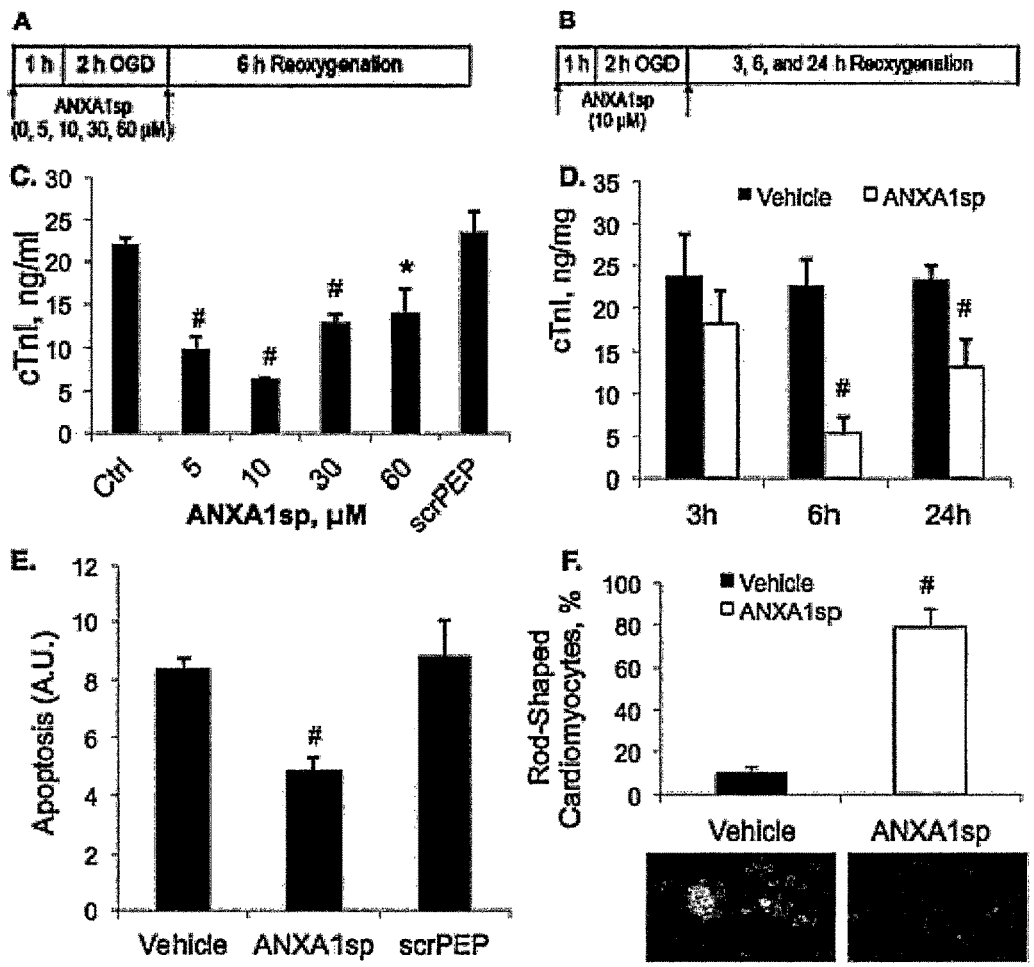
FIG. 1. ANXA1sp prevents in vitro adult rat ventricular cardiomyocyte (ARVC) death following hypoxia-reoxygenation (by oxygen and glucose deprivation, OGD) over a range of concentrations (A) and reoxygenation time points (B). Dose-finding experiment (A): ARVCs incubated with a range of ANXA1sp doses, underwent 2 h OGD, followed by 6 h reoxygenation. Time-course experiment (B): ARVCs incubated with 10 µM ANXA1sp underwent 2 h OGD and reoxygenation for 3, 6 or 24 h. Cytoprotective effects include reduced cardiac Troponin I (cTnI) release in the medium (high sensitivity ELISA assay, Life Diagnostics, C, D), increased percentage of characteristic rod-shaped viable cardiomyocytes (F), and reduced cardiomyocyte apoptosis (Cell Death Detection ELISA, Roche, E). Results presented as mean±SD. *$P<0.05$ and #$P<0.01$ versus vehicle treated control (n=3 cardiomyocyte preparations/dose and time point). scrPEP, scrambled peptide; Ctrl, vehicle control.

The present invention is based on the unexpected discovery that an ANXA1 peptide (e.g., ANXA1 tripeptide or ANXA1 short peptide (ANXA1sp)) can increase the amount and/or activity of one or more than one SIRT. In some embodiments, the SIRT is SIRT3. Thus, in one embodiment, the present invention provides a method of increasing the amount and/or the activity of one or more than one SIRT in a subject (e.g., a subject in need thereof), comprising administering to the subject an effective amount of ANXA1 peptide (e.g., an ANXA1 short peptide, also called ANXA1 tripeptide (ANXA1sp)).

A subject of this invention can be a subject that has, is suspected of having, or is at increased risk of having a SIRT-associated cancer, type 2 diabetes, a metabolic disorder, obesity, a fat-related metabolic disorder, a neurodegenerative disorder, a disorder resulting in cognitive decline, a spinal cord injury, a blood coagulation disorder, an ocular disorder, a respiratory disorder, a viral infection, a fungal infection, chronic hepatitis infection, an autoimmune disorder, flushing, a mitochondrial disease or disorder, a chemotherapy-induced neuropathy, neuropathy associated with an ischemic event, cardiovascular disease, a disorder associated with aging, a disorder associated with stress, stroke, arthritis, hypertension, Alzheimer's disease, liver disease, a disorder that would benefit from increased mitochondrial activity, an inflammatory disorder, muscle tissue damage associated with hypoxia or ischemia, trauma, ischemia, chronic pain (e.g., trauma, ischemia and/or chronic pain associated with brain and/or spinal cord disease, damage and/or injury) and any combination thereof.

In a further embodiment, the present invention provides a method of increasing the lifespan and/or health span of a subject, delaying cellular senescence of cells in a subject, preventing apoptosis of cells in a subject, mimicking the effects of caloric restriction in a subject and/or increasing resistance of cells to stress in a subject, comprising administering to the subject an amount of an ANXA1 peptide (e.g., ANXA1sp) that is effective in increasing the amount and/or activity of one or more than one SIRT in the subject, thereby increasing the lifespan or health span of the subject, delaying cellular senescence of cells in the subject, preventing apoptosis of cells in the subject, mimicking the effects of caloric restriction in the subject and/or increasing resistance of cells to stress in the subject, in any combination.

Additionally provided herein is a method of treating a skin disorder and/or inhibiting the effects of ageing on skin cells in a subject, comprising contacting the skin cells of the subject with an amount of an ANXA1 peptide (e.g., ANXA1sp) that is effective in increasing the amount and/or activity of one or more than one SIRT in the skin cells, thereby treating a skin disorder and/or inhibiting the effects of ageing on skin cells in the subject.

The methods of this invention can further comprise the step of administering a therapeutic agent prior to, concurrent with and/or after administration of the ANXA1 peptide (e.g., ANXA1sp).

The present invention also provides a method of enhancing muscle performance and/or improving physical endurance in a subject, comprising administering to the subject an amount of an ANXA1 peptide (e.g., ANXA1sp, ANXA1 tripeptide) effective in increasing the amount and/or activity of one or more than one SIRT in the subject, thereby enhancing muscle performance and/or improving physical endurance in the subject.

A further embodiment of this invention is a method of increasing the lifespan of a cell, comprising contacting the cell with an amount of an ANXA1 peptide (e.g., ANXA1sp, an ANXA1 tripeptide) effective in increasing the amount and/or activity of one or more SIRT in the cell, thereby increasing the lifespan of the cell.

In the methods of this invention that involve a cell, the cell can be in vitro, ex vivo or in vivo. In some embodiments, the cell can be a cell for transplantation, a cell for cell therapy, an embryonic stem cell, a pluripotent cell, a bone marrow cell, etc., singly or in any combination. Such methods can further comprise contacting the cell with a therapeutic agent, before, during and/or after contacting the cell with the ANXA1 peptide (e.g., ANXA1sp; ANXA1 tripeptide), in any combination.

In the methods, kits and compositions of this invention, the sirtuin can be Sirtuin 1 (SIRT1), Sirtuin 2 (SIRT2), Sirtuin 3 (SIRT3), Sirtuin 4 (SIRT4), Sirtuin 5 (SIRT5), Sirtuin 6 (SIRT6) and/or Sirtuin 7 (SIRT7), singly or in any combination.

The present invention also provides a kit for increasing the amount and/or activity of one or more than one sirtuin in a subject in need thereof, comprising an ANXA1 peptide (e.g., ANXA1sp) and instructions for use.

Further aspects include the use of an ANXA1 peptide (e.g., ANXA1sp) in the manufacture of a medicament for the treatment of a SIRT-associated disorder of this invention in a subject in need thereof.

Any patents, patent publications and non-patent publications mentioned in this specification are indicative of the level of those skilled in the art to which the invention pertains. These patents and publications are herein incorporated by reference to the same extent as if each individual patent or publication was specifically and individually indicated to be incorporated by reference.

For the purposes of promoting an understanding of the principles of the present invention, reference will now be made to various embodiments and specific language will be used to describe the same. It will nevertheless be understood that no limitation of the scope of the invention is thereby intended, such alteration and further modifications of the invention as illustrated herein, being contemplated as would normally occur to one skilled in the art to which the invention relates.

The terms "a," "an" and "the" are used herein to refer to one or to more than one (i.e., at least one) of the grammatical object of the article. By way of example, "an element" means at least one element and can include more than one element (e.g., a multiplicity or plurality of elements).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, "one or more" or "one or more than one" can mean one, two, three, four, five, six, seven, eight, nine, ten or more, up to any number.

Unless otherwise defined, all technical terms used herein have the same meaning as commonly understood by one of ordinary skill in the art to which this disclosure belongs.

As used herein, the term "subject" and "patient" are used interchangeably herein and refer to both human and nonhuman animals. The term "nonhuman animals" includes all vertebrates, e.g., mammals and non-mammals, such as non-human primates, sheep, dog, pig, cat, horse, cow, chickens, amphibians, reptiles, rodents (e.g., mice, rats, etc.) and the like. In particular embodiments, the subject of this invention is a human subject.

A "subject in need thereof" or "a subject in need of" is a subject known to have, or is suspected of having or developing a sirtuin-associated disorder or sirtuin-associated condition of this invention or is at risk of having or developing a sirtuin-associated disorder or sirtuin-associated condition as described herein. By "sirtuin-associated" is meant that the disease, disorder or condition is caused by or results directly or indirectly from an amount and/or activity of a sirtuin that is abnormal, dysregulated, decreased and/or aberrant (e.g., in a subject) as compared with the amount and/or activity of the sirtuin in the absence of the disease, disorder or condition (e.g., in a subject).

The term "administering" or "administered" as used herein is meant to include topical, parenteral and/or oral administration, all of which are described herein. Parenteral administration includes, without limitation, intravenous, subcutaneous and/or intramuscular administration (e.g., skeletal muscle or cardiac muscle administration). In the methods of this invention, the peptide of this invention may be administered alone and/or simultaneously with one or more other compounds. In some embodiments, the compounds may be administered sequentially, in any order. It will be appreciated that the actual method and order of administration will vary according to, inter alia, the particular preparation of compound(s) being utilized, and the particular formulation(s) of the one or more other compounds being utilized. The optimal method and order of administration of the compounds of the invention for a given set of conditions can be ascertained by those skilled in the art using conventional techniques and in view of the information set out herein.

The term "administering" or "administered" also refers, without limitation, to oral, sublingual, buccal, transnasal, transdermal, rectal, intramascular, intravenous, intraarterial (intracoronary), intraventricular, intrathecal, and subcutaneous routes. In accordance with good clinical practice, the compounds of this invention can be administered at a dose that will produce effective beneficial effects without causing undue harmful or untoward side effects, i.e., the benefits associated with administration outweigh the detrimental effects.

Also as used herein, the terms "treat," "treating" or "treatment" refer to any type of action that imparts a modulating effect, which, for example, can be a beneficial and/or therapeutic effect, to a subject afflicted with a condition, disorder, disease or illness, including, for example, improvement in the condition of the subject (e.g., in one or more symptoms), delay in the progression of the disorder, disease or illness, delay of the onset of the disease, disorder, or illness, and/or change in clinical parameters of the condition, disorder, disease or illness, etc., as would be well known in the art.

An "effective amount" or "therapeutically effective amount" refers to an amount of a compound or composition of this invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an effective amount or therapeutically effective amount in any individual case can be determined by one of ordinary skill in the art by reference to the pertinent texts and literature and/or by using routine experimentation. (See, for example, Remington, The Science and Practice of Pharmacy (latest edition)).

As used herein, the term "ameliorate" refers to the ability to make better, or more tolerable, a condition, disorders and/or symptom. The term "prevent" refers to the ability to keep a condition, a reaction, a disorder and/or symptom from happening or existing or developing.

Human ANXA1 has a molecular weight of about 37 kDa and consists of about 346 amino acids. The amino acid sequence is coded for by nucleotides 75-1115 of the nucleotide sequence of GenBank® Accession number X05908 (SEQ ID NO:1) and is known by one skilled in the art as having the amino acid sequence of GenBank® Accession number P04083 (SEQ ID NO:2) (said sequences are incorporated by reference herein).

As used herein, the term "ANXA1 peptides" or "annexin A1 peptides" are peptide fragments of annexin 1, and are shorter than the full length ANXA1 protein (e.g., at least about 1, 2, 3, 4, 5, 6, 7, 8, 9, 10, 15, 20, 25, 30, 40, 50, 60, 70, 80, 90, 100, 125, 150, 175, 200, 225, 250, 275, 300, 325, 326, 327, 328, 329, 300, 331, 332, 333, 334, 335, 336, 337, 338, 339, 340, 341, 342, 434, 344, or 345 amino acids shorter), which have similar biological effects as ANXA1 on a cell, which biological activities are known in the art and as described herein. ANXA1 peptides may optionally be acetylated (Ac-) at the N-terminal amino acid residue. ANXA1 peptides include, but are not limited to, the ANXA1sp, Ac-Gln-Ala-Trp, the peptide Ac-Lys-Gln-Ala-Trp (SEQ ID NO:3); the peptide Ac-Phe-Leu-Lys, the peptide Ac-Phe-Gln-Ala-Trp (SEQ ID NO:4), the peptide Ac-Phe-Leu-Lys-Gln-Ala-Trp (SEQ ID NO:5), the peptide Glu-Phe-Leu-Lys-Gln-Ala-Trp (SEQ ID NO:6), the peptide Phe-Gln-Ala-Trp (SEQ ID NO:4), the peptide Phe-Leu-Lys-Gln-Ala-Trp (SEQ ID NO:7), the peptide Ac-Ala-Met-Val-Ser-Glu-Phe-Leu-Lys-Gln-Ala-Trp (SEQ ID NO:8), the peptide Ala-Met-Val-Ser-Glu-Phe-Leu-Lys-Gln-Ala-Trp (SEQ ID NO:8), the peptide Ac-Val-Ser-Glu-Phe-Leu-Lys-Gln-Ala-Trp (SEQ ID NO:9) or other fragments of annexin 1 singly or in any combination, as long as they maintain the annexin 1 functionality. As used herein, the term "Ac2-26" refers to a 25mer peptide derived from annexin 1 having the sequence Ac-Ala-Met-Val-Ser-Glu-Phe-Leu-Lys-Gln-Ala-Trp-Phe-Ile-Glu-Asn-Glu-Glu-Gln-Glu-Tyr-Val-Gln-Tyr-Val-Lys (SEQ ID NO:10). As used herein, the term "ANXA1sp" or "annexin 1 short peptide" or "ANXA1 tripeptide" refers to the 3mer peptide derived from ANXA1 having the sequence: Ac-Gln-Ala-Trp.

"SIRT1 protein" refers to a member of the sir2 family of sirtuin deacetylases. In one embodiment, a SIRT1 protein includes yeast Sir2 (GenBank Accession No. P53685), *C. elegans* Sir-2.1 (GenBank Accession No. NP_501912), human SIRT1 (GenBank Accession No. NM_012238 or NP_036370 (or AF083106)), and equivalents and fragments thereof. In another embodiment, a SIRT1 protein includes a polypeptide comprising a sequence consisting of, or consisting essentially of, the amino acid sequence set forth in GenBank Accession Nos. NP_036370, NP_501912, NP_085096, NP_036369, or P53685. SIRT1 proteins include polypeptides comprising all or a portion of the amino acid sequence set forth in GenBank Accession Nos. NP_036370, NP_501912, NP_085096, NP_036369, or P53685; the amino acid sequence set forth in GenBank Accession Nos. NP_036370, NP_501912, NP_085096, NP_036369, or P53685 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. NP_036370, NP_501912, NP_085096, NP_036369, or P53685, and functional fragments thereof. Polypeptides of the invention also include homologs (e.g., orthologs and paralogs), variants, or fragments, of GenBank Accession Nos. NP_036370, NP_501912, NP_085096, NP_036369, or P53685.

As used herein "SIRT2 protein," "SIRT3 protein," "SIRT4 protein," SIRT 5 protein," "SIRT6 protein," and "SIRT7 protein" refer to other mammalian, e.g., human, sirtuin deacetylase proteins that are homologous to SIRT1 protein, particularly in the approximately 275 amino acid conserved catalytic domain. For example, SIRT3 protein refers to a member of the sirtuin deacetylase protein family that is homologous to a SIRT1 protein. In one embodiment, a SIRT3 protein includes human SIRT3 (GenBank Accession No. AAH01042, NP_036371, or NP_001017524) and mouse SIRT3 (GenBank Accession No. NP_071878) proteins, and equivalents and fragments thereof. In another embodiment, a SIRT3 protein includes a polypeptide comprising a sequence consisting of, or consisting essentially of, the amino acid sequence set forth in GenBank Accession Nos. AAH01042, NP_036371, NP_001017524, or NP_071878. SIRT3 proteins include polypeptides comprising all or a portion of the amino acid sequence set forth in GenBank Accession AAH01042, NP_036371, NP_001017524, or NP_071878; the amino acid sequence set forth in GenBank Accession Nos. AAH01042, NP_036371, NP_001017524, or NP_071878 with 1 to about 2, 3, 5, 7, 10, 15, 20, 30, 50, 75 or more conservative amino acid substitutions; an amino acid sequence that is at least 60%, 70%, 80%, 90%, 95%, 96%, 97%, 98%, or 99% identical to GenBank Accession Nos. AAH01042, NP_036371, NP_001017524, or NP_071878, and functional fragments thereof. Polypeptides of the invention also include homologs (e.g., orthologs and paralogs), variants, or fragments, of GenBank Accession Nos. AAH01042, NP_036371, NP_001017524, or NP_071878.

As described herein, the invention provides methods for using ANXA1 peptides, or compositions comprising ANXA1 peptides (e.g., ANXA1sp) for increasing the amount and/or activity (e.g., $NAD^+$-dependent protein deaetylase/ADP ribosyltransferase activity) of one or more than one SIRT protein. The ANXA1 peptide and compositions comprising an ANXA1 peptide of this invention can be used for a variety of therapeutic applications including, for example, increasing the lifespan of a cell, and treating and/or inhibiting a wide variety of diseases and disorders and conditions associated with aberrant amounts and/or activity of a sirtuin, including, for example, diseases or disorders related to aging or stress, diabetes, obesity, neurodegenerative diseases, chemotherapeutic induced neuropathy, neuropathy associated with an ischemic event, ocular diseases and/or disorders, cardiovascular disease, blood clotting disorders, inflammation, and/or flushing, etc. ANXA1 peptides that increase the level and/or activity of a sirtuin protein may also be used for treating a disease or disorder in a subject that would benefit from increased mitochondrial activity, for enhancing muscle performance, for increasing muscle ATP levels, and/or for treating, reducing or inhibiting muscle tissue damage associated with hypoxia or ischemia.

In some embodiments, the ANXA1 peptides described herein may be administered alone or in combination with other compounds. In one embodiment, an ANXA1 peptide that increases the level and/or activity of a SIRT protein may be administered with one or more of the following compounds: resveratrol, lutein, fisetin, piceatannol, nicotinic acid and quercetin, singly or in any combination. In some embodiments, the ANXA1 peptide of this invention can be administered with one or more therapeutic agents for the treatment or prevention of various diseases, including, for example, cancer, diabetes, neurodegenerative diseases, cardiovascular disease, blood clotting, inflammation, flushing, obesity, aging, stress, etc.

In various embodiments, a combination therapy comprising an ANXA1 peptide can refer to (1) a pharmaceutical composition that comprises one or more ANXA1 peptides in combination with one or more therapeutic agents (e.g., one or more therapeutic agents described herein); and (2) co-administration of one or more ANXA1 peptides with one or more therapeutic agents wherein the ANXA1 peptide(s) and therapeutic agent(s) have not been formulated in the same compositions (but may be present within the same kit or package, such as a blister pack or other multi-chamber package; connected, separately sealed containers (e.g., foil pouches) that can be separated by the user; or a kit where the ANXA1 peptide(s) and other therapeutic agent(s) are in separate vessels or containers). When using separate formulations, the ANXA1 peptide(s) can be administered at the same time as, intermittently, staggered, prior to, subsequent to, or combinations thereof, with respect to the administration of a therapeutic agent or agents.

In some embodiments, the present invention provides a method of extending the lifespan of a cell and/or health span of a subject, extending the proliferative capacity of a cell, slowing aging of a cell, promoting the survival of a cell, delaying cellular senescence in a cell, mimicking the effects of calorie restriction in a subject, increasing the resistance of a cell to stress, and/or preventing, reducing or inhibiting apoptosis of a cell, by contacting the cell with an ANXA1 peptide of the invention that increases the level and/or activity of one or more than one SIRT protein. In an exemplary embodiment, the methods comprise contacting the cell with and/or administering to a subject, an ANXA1 peptide of this invention.

In some embodiments, the methods of this invention can be used to increase the amount of time that cells, particularly primary cells (i.e., cells obtained from an organism, e.g., a human), can be kept alive ex vivo or in vitro (e.g., in a cell culture). Embryonic stem (ES) cells and pluripotent cells, and cells differentiated therefrom, can also be treated with an ANXA1 peptide of this invention that increases the level and/or activity of one or more than one SIRT protein to keep the cells, and/or progeny thereof, in culture for longer periods of time. Such cells can also be used for transplantation into a subject, e.g., after ex vivo modification.

In some embodiments, cells that are intended to be preserved for long periods of time may be treated with an ANXA1 peptide of this invention that increases the level and/or activity of a SIRT protein. The cells may be in suspension (e.g., blood cells, serum, biological growth medium, etc.) and/or in tissues or organs. For example, blood collected from an individual for purposes of transfusion may be treated with an ANXA1 peptide of this invention that increases the level and/or activity of a SIRT protein to preserve the blood cells for longer periods of time. Additionally, blood to be used for forensic purposes may also be preserved using an ANXA1 peptide of this invention that increases the level and/or activity of a SIRT protein. Other cells that may be treated to extend their lifespan or protect against apoptosis include cells for consumption, e.g., cells from non-human mammals (such as meat) or plant cells (such as vegetables).

ANXA1 peptides of this invention that increase the level and/or activity of a SIRT protein can also be applied during developmental and growth phases in mammals, plants, insects or microorganisms, in order to, e.g., alter, modulate or accelerate the developmental and/or growth process.

In some embodiments, ANXA1 peptides of this invention that increase the level and/or activity of a SIRT protein can be used to treat cells useful for transplantation or cell therapy, including, for example, solid tissue grafts, organ transplants, cell suspensions, stem cells, bone marrow cells, etc. The cells or tissue can be an autograft, an allograft, a syngraft or a xenograft. The cells or tissue can be treated with the ANXA1 peptide prior to administration/implantation, concurrently with administration/implantation, and/or post administration/implantation into a subject. The cells or tissue can be treated prior to removal of the cells from the donor, ex vivo after removal of the cells or tissue from the donor, and/or post implantation into the recipient. For example, the donor or recipient can be treated systemically with an ANXA1 peptide of this invention or can have a subset of cells/tissue treated locally with an ANXA1 peptide that increases the level and/or activity of a SIRT protein. In certain embodiments, the cells or tissue (or donor/recipient) can additionally be treated with one or more than one therapeutic agent useful for prolonging graft survival, such as, for example, an immunosuppressive agent, a cytokine, an angiogenic factor, etc., as are known in the art.

In yet other embodiments, cells can be treated with ANXA1 peptide of this invention that increases the level and/or activity of a SIRT protein in vivo, e.g., to increase the lifespan or prevent, inhibit or reduce apoptosis of the cells. For example, skin can be protected from aging (e.g., developing wrinkles, loss of elasticity, etc.) by treating skin and/or epithelial cells with an ANXA1 peptide of this invention that increases the level and/or activity of a SIRT protein. In an exemplary embodiment, skin is contacted with a pharmaceutical or cosmetic composition comprising an ANXA1 peptide of this invention that increases the level and/or activity of a SIRT protein. Exemplary skin afflictions or skin conditions that may be treated in accordance with the methods described herein include disorders or diseases associated with or caused by inflammation, sun damage or natural aging. For example, the compositions and methods of this invention can be used for prevention, inhibition, reduction and/or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, an ANXA1 peptide of this invention that increases the level and/or activity of a SIRT protein can be used as a formulation for the treatment of wounds and/or burns to promote healing, including, for example, first-, second- or third-degree burns and/or thermal, chemical or electrical burns. The formulations comprising the ANXA1 peptide of this invention can be administered, e.g., topically to the skin and/or mucosal tissue.

Topical formulations comprising an ANXA1 peptide of this invention that increases the level and/or activity of a SIRT protein may also be used in prophylactic or preventive, e.g., chemopreventive, compositions. When used in a prophylactic or preventive method, susceptible skin or tissue is treated prior to any visible condition in a particular individual.

ANXA1 peptides of this invention can be delivered locally or systemically to a subject. In some embodiments, an ANXA1 peptide of this invention can be delivered locally to a tissue or organ of a subject by injection, topical formulation, etc.

In another embodiment, an ANXA1 peptide of this invention that increases the level and/or activity of a SIRT protein can be used for treating and/or inhibiting or preventing a disease or condition induced or exacerbated by cellular senescence in a subject; methods for decreasing the rate of senescence of a subject, e.g., after onset of senescence; methods for extending the lifespan of a cell and/or subject; methods for treating and/or preventing or inhibiting a disease or condition relating to lifespan; methods for treating and/or preventing or inhibiting a disease or condition relating to the proliferative capacity of cells; and methods for treating and/or preventing or inhibiting a disease or condition resulting from cell damage or cell death.

In some embodiments, an ANXA1 peptide of this invention that increases the level and/or activity of a SIRT protein can be administered to a subject to increase the lifespan of cells of the subject and/or to protect cells of the subject against stress and/or against apoptosis.

ANXA1 peptides of this invention that increase the level and/or activity of a SIRT protein can be administered to a subject to prevent or inhibit or delay aging and aging-related consequences or diseases, such as stroke, heart disease, heart failure, arthritis, high blood pressure, and/or neurodegenerative disorders, such as Alzheimer's disease. Other non-limiting examples of conditions that can be treated include ocular disorders, e.g., associated with the aging of the eye, such as cataracts, glaucoma, and/or macular degeneration. ANXA1 peptides of this invention that increase the level and/or activity of a SIRT protein can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotrophic lateral sclerosis, and muscular dystrophy; AIDS; fulminant hepatitis; diseases linked to degeneration of the brain, such as Creutzfeldt-Jakob disease, retinitis pigmentosa and cerebellar degeneration; myelodysplasia such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to ultraviolet UV irradiation; lichen planus; atrophy of the skin; cataract; and graft rejections. Cell death can also be caused by surgery, drug therapy, chemical exposure or radiation exposure.

ANXA1 peptides of this invention that increase the level and/or activity of a SIRT protein can also be administered to a subject that has an acute disease, e.g., damage to an organ or tissue, e.g., a subject with liver disease, a subject that has had or is having a stroke or myocardial infarction or a subject that has had a brain and/or spinal cord injury (e.g., to treat ischemia, trauma and/or chronic pain associated with a brain and/or spinal cord injury).

In another embodiment, the invention provides a method for treating and/or preventing a cardiovascular disease by administering to a subject in need thereof an ANXA1 peptide of this invention that increases the level and/or activity of one or more than one SIRT protein.

Cardiovascular diseases that can be treated or prevented using the ANXA1 peptides of this invention that increase the level and/or activity of a SIRT protein include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable or preventable using ANXA1 peptides and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated or prevented include those related to platelet aggregation, the retinal arterioles, the glomerular arterioles, the vasa nervorum, cardiac arterioles, and associated capillary beds of the eye, the kidney, the heart, and the central and peripheral nervous systems. The ANXA1 peptides that increase the level and/or activity of a SIRT protein may also be used for increasing HDL levels in plasma of a subject.

Yet other disorders that may be treated with an ANXA1 peptide of this invention that increases the level and/or activity of a SIRT protein include restenosis, e.g., following coronary intervention, and disorders relating to an abnormal level of high density and low density cholesterol.

In one embodiment, an ANXA1 peptide of this invention that increases the level and/or activity of a SIRT protein may be administered as part of a combination therapeutic with another cardiovascular agent. In one embodiment, an ANXA1 peptide of this invention that increases the level and/or activity of a SIRT protein may be administered as part of a combination therapeutic with an anti-arrhythmia agent. In another embodiment, an ANXA1 peptide of this invention that increases the level and/or activity of a SIRT protein may be administered as part of a combination therapeutic with another cardiovascular agent.

ANXA1 peptides that increase the level and/or activity of a SIRT protein may be administered to subjects who have recently received or are likely to receive a dose of radiation or toxin. In one embodiment, the dose of radiation or toxin is received as part of a work-related or medical procedure, e.g., administered as a prophylactic measure. In another embodiment, the radiation or toxin exposure is received unintentionally. In such a case, the ANXA1 peptide can be administered as soon as possible after the exposure to inhibit apoptosis and the subsequent development of acute radiation syndrome.

In some embodiments, ANXA1 peptides that increase the level and/or activity of a SIRT protein may be used for treating and/or preventing cancer. Calorie restriction has been linked to a reduction in the incidence of age-related disorders including cancer. Accordingly, an increase in the level and/or activity of a SIRT protein may be useful for treating and/or preventing the incidence of age-related disorders, such as, for example, cancer. Exemplary cancers that may be treated using an ANXA1 peptide of this invention are those of the brain and kidney; hormone-dependent cancers including breast, prostate, testicular, and ovarian cancers; lymphomas, and/or leukemias. In cancers associated with solid tumors, an ANXA1 peptide can be administered directly into the tumor. Cancer of the blood cells, e.g., leukemia, can be treated by administering an ANXA1 peptide of this invention into the blood stream or into the bone marrow. Benign cell growth, e.g., warts, can also be treated. Other diseases that can be treated include autoimmune diseases, e.g., systemic lupus erythematosus, scleroderma, and arthritis, in which autoimmune cells should be removed. Viral infections such as herpes, human immunodeficiency virus (HIV), adenovirus, and HTLV-1 associated malignant and benign disorders can also be treated by administration of an ANXA1 peptide of this invention. Alternatively, cells can be obtained from a subject, treated ex vivo to remove or eliminate certain undesirable cells, e.g., cancer cells, and administered back to the same or a different subject.

Chemotherapeutic agents can be administered prior to, during and/or after administration of an ANXA1 peptide of this invention. In addition to conventional chemotherapeutics, the ANXA1 peptides of this invention can also be used with antisense RNA, RNAi or other polynucleotides to inhibit the expression of the cellular components that contribute to unwanted cellular proliferation.

Combination therapies comprising an ANXA1 peptide of this invention and a conventional chemotherapeutic agent may be advantageous over combination therapies known in the art because the combination allows the conventional chemotherapeutic agent to exert greater effect at lower dosage. In some embodiments, the effective dose ($ED_{50}$) for a chemotherapeutic agent, or combination of conventional chemotherapeutic agents, when used in combination with an ANXA1 peptide of this invention can be at least 2 fold less than the $ED_{50}$ for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with an ANXA1 peptide of this invention can be at least 2 fold greater than the TI for conventional chemotherapeutic regimen alone, and even 5 fold, 10 fold or even 25 fold greater.

In certain aspects, ANXA1 peptides of this invention that increase the level and/or activity of a SIRT protein can be used to treat patients suffering from neurodegenerative diseases, and traumatic or mechanical injury to the central nervous system (CNS), spinal cord or peripheral nervous system (PNS). Neurodegenerative disease typically involves reductions in the mass and volume of the human brain, which may be due to the atrophy and/or death of brain cells, which are far more profound than those in a healthy person that are attributable to aging. Nonlimiting examples of neurodegenerative diseases include, but are not limited to, Alzheimer's disease (AD), Parkinson's disease (PD), Huntington's disease (HD), amyotrophic lateral sclerosis (ALS; Lou Gehrig's disease), diffuse Lewy body disease, choreaacanthocytosis, primary lateral sclerosis, ocular diseases (ocular neuritis), chemotherapy-induced neuropathies (e.g., from vincristine, paclitaxel, bortezomib), diabetes-induced neuropathies, chronic pain and Friedreich's ataxia. ANXA1 peptides of this invention that increase the level and/or activity of a SIRT protein can be used to treat these disorders and others as described below.

AD is a CNS disorder that results in memory loss, unusual behavior, personality changes, and a decline in thinking abilities. These losses are related to the death of specific types of brain cells and the breakdown of connections and their supporting network (e.g., glial cells) between them. The earliest symptoms include loss of recent memory, faulty judgment, and changes in personality.

PD is a CNS disorder that results in uncontrolled body movements, rigidity, tremor, and dyskinesia, and is associated with the death of brain cells in an area of the brain that produces dopamine.

ALS (motor neuron disease) is a CNS disorder that attacks the motor neurons, components of the CNS that connect the brain to the skeletal muscles.

HD is a neurodegenerative disease that causes uncontrolled movements, loss of intellectual faculties, and emotional disturbance.

Tay-Sachs disease and Sandhoff disease are glycolipid storage diseases where GM2 ganglioside and related glycolipid substrates for β-hexosaminidase accumulate in the nervous system and trigger acute neurodegeneration.

It is well-known that apoptosis plays a role in AIDS pathogenesis in the immune system. However, HIV-1 also induces neurological disease, which can be treated with the ANXA1 peptides of the invention.

Neuronal loss is also a salient feature of prion diseases, such as Creutzfeldt-Jakob disease in human, BSE in cattle (mad cow disease), Scrapie Disease in sheep and goats, and feline spongiform encephalopathy (FSE) in cats. ANXA1 peptides of this invention that increase the level and/or activity of a SIRT protein may be useful for treating or preventing neuronal loss due to these prior diseases.

In another embodiment, an ANXA1 peptide of this invention that increases the level and/or activity of a SIRT protein may be used to treat or prevent any disease or disorder involving axonopathy. Distal axonopathy is a type of peripheral neuropathy that results from some metabolic or toxic derangement of peripheral nervous system (PNS) neurons. It is the most common response of nerves to metabolic or toxic disturbances, and as such may be caused by metabolic diseases such as diabetes, renal failure, deficiency syndromes such as malnutrition and alcoholism, or the effects of toxins or drugs. Those with distal axonopathies usually present with symmetrical glove-stocking sensori-motor disturbances. Deep tendon reflexes and autonomic nervous system (ANS) functions are also lost or diminished in affected areas.

Diabetic neuropathies are neuropathic disorders that are associated with diabetes mellitus. Relatively common conditions which may be associated with diabetic neuropathy include third nerve palsy; mononeuropathy; mononeuritis multiplex; diabetic amyotrophy; a painful polyneuropathy; autonomic neuropathy; and thoracoabdominal neuropathy.

Peripheral neuropathy is the medical term for damage to nerves of the peripheral nervous system, which may be caused either by diseases of the nerve or from the side-effects of systemic illness. Major causes of peripheral neuropathy include seizures, nutritional deficiencies, and HIV, though diabetes is the most likely cause.

In an exemplary embodiment, an ANXA1 peptide of this invention that increases the level and/or activity of a SIRT protein may be used to treat or prevent multiple sclerosis (MS), including relapsing MS and monosymptomatic MS, and other demyelinating conditions, such as, for example, chronic inflammatory demyelinating polyneuropathy (CIDP), or symptoms associated therewith.

In yet another embodiment, an ANXA1 peptide of this invention that increases the level and/or activity of a SIRT protein may be used to treat trauma to the nerves, including, trauma due to disease, injury (including surgical intervention), or environmental trauma (e.g., neurotoxins, alcoholism, etc.).

ANXA1 peptides of this invention that increase the level and/or activity of a SIRT protein may also be useful to prevent, treat, and alleviate symptoms of various peripheral nervous system (PNS) disorders. The term "peripheral neuropathy" encompasses a wide range of disorders in which the nerves outside of the brain and spinal cord—peripheral nerves—have been damaged. Peripheral neuropathy may also be referred to as peripheral neuritis, or if many nerves are involved, the terms polyneuropathy or polyneuritis may be used.

PNS diseases treatable with ANXA1 peptides of this invention that increase the level and/or activity of a SIRT protein include: diabetes, leprosy, Charcot-Marie-Tooth disease, Guillain-Barre syndrome and brachial plexus neuropathies (diseases of the cervical and first thoracic roots, nerve trunks, cords, and peripheral nerve components of the brachial plexus).

In some embodiments, an ANXA1 peptide of this invention can be used to treat and/or prevent a polyglutamine disease. Exemplary polyglutamine diseases include spinobulbar muscular atrophy (Kennedy disease), Huntington's Disease (HD), dentatorubral-pallidoluysian atrophy (Haw River syndrome), spinocerebellar ataxia type 1, spinocerebellar ataxia type 2, spinocerebellar ataxia type 3 (Machado-Joseph disease), spinocerebellar ataxia type 6, spinocerebellar ataxia type 7, and spinocerebellar ataxia type 17.

In certain embodiments, the invention provides a method to treat a central nervous system cell to prevent damage in response to a decrease in blood flow to the cell. Typically the severity of damage that may be prevented will depend in large part on the degree of reduction in blood flow to the cell and the duration of the reduction. In one embodiment, apoptotic or necrotic cell death may be prevented. In another embodiment, ischemic-mediated damage, such as cytoxic edema or central nervous system tissue anoxemia, may be prevented. In each embodiment, the central nervous system cell may be a spinal cell or a brain cell.

Another aspect encompasses administering an ANXA1 peptide of this invention to a subject to treat a central nervous system ischemic condition. A number of central nervous system ischemic conditions may be treated by the ANXA1 peptides described herein. In one embodiment, the ischemic condition is a stroke that results in any type of ischemic central nervous system damage, such as apoptotic or necrotic cell death, cytoxic edema or central nervous system tissue anoxia. The stroke may impact any area of the brain or be caused by any etiology commonly known to result in the occurrence of a stroke. In one alternative of this embodiment, the stroke is a brain stem stroke. In another alternative of this embodiment, the stroke is a cerebellar stroke. In still another embodiment, the stroke is an embolic stroke. In yet another alternative, the stroke may be a hemorrhagic stroke. In a further embodiment, the stroke is a thrombotic stroke.

In yet another aspect, an ANXA1 peptide of this invention can be administered to reduce infarct size of the ischemic core following a central nervous system ischemic condition. Moreover, an ANXA1 peptide of this invention can be beneficially administered to reduce the size of the ischemic penumbra or transitional zone following a central nervous system ischemic condition.

In one embodiment, a combination drug regimen may include drugs or compounds for the treatment or prevention or inhibition or delay of onset of neurodegenerative disorders or secondary conditions associated with these conditions. Thus, a combination drug regimen may include one or more ANXA1 peptides and one or more anti-neurodegeneration agents.

In other aspects, ANXA1 peptides of this invention that increase the level and/or activity of a SIRT protein can be used to treat or prevent blood coagulation disorders (or hemostatic disorders). As used interchangeably herein, the terms "hemostasis," "blood coagulation," and "blood clotting" refer to the control of bleeding, including the physiological properties of vasoconstriction and coagulation. Blood coagulation assists in maintaining the integrity of mammalian circulation after injury, inflammation, disease, congenital defect, dysfunction or other disruption. Further, the formation of blood clots does not only limit bleeding in case of an injury (hemostasis), but may lead to serious organ damage and death in the context of atherosclerotic diseases by occlusion of an important artery or vein. Thrombosis is thus blood clot formation at the wrong time and place.

Accordingly, the present invention provides anticoagulation and antithrombotic treatments aiming at inhibiting the formation of blood clots in order to prevent or treat blood coagulation disorders, such as myocardial infarction, stroke, loss of a limb by peripheral artery disease or pulmonary embolism.

As used interchangeably herein, "modulating or modulation of hemostasis" and "regulating or regulation of hemostasis" includes the induction (e.g., stimulation or increase) of hemostasis, as well as the inhibition (e.g., reduction or decrease) of hemostasis.

In one aspect, the invention provides a method for reducing or inhibiting hemostasis in a subject by administering an ANXA1 peptide of this invention that increases the level and/or activity of a SIRT protein. The ANXA1 peptide and methods disclosed herein are useful for the treatment or prevention or inhibition of thrombotic disorders. As used herein, the term "thrombotic disorder" includes any disorder or condition characterized by excessive or unwanted coagulation or hemostatic activity, or a hypercoagulable state. Thrombotic disorders include diseases, or disorders involving platelet adhesion and thrombus formation, and may manifest as an increased propensity to form thromboses, e.g., an increased number of thromboses, thrombosis at an early age, a familial tendency towards thrombosis, and thrombosis at unusual sites.

In another embodiment, a combination drug regimen may include drugs or compounds for the treatment or prevention of blood coagulation disorders or secondary conditions associated with these conditions. Thus, a combination drug regimen may include one or more ANXA1 peptides of this invention that increase the level and/or activity of a sirtuin protein and one or more anti-coagulation or anti-thrombosis agents.

In another aspect, ANXA1 peptides of this invention that increase the level and/or activity of a SIRT protein may be used for treating or preventing or inhibiting weight gain or obesity in a subject. For example, ANXA1 peptides of this invention that increase the level and/or activity of a sirtuin protein may be used, for example, to treat or prevent or inhibit hereditary obesity, dietary obesity, hormone related obesity, obesity related to the administration of medication, to reduce the weight of a subject, or to reduce or prevent weight gain in a subject. A subject in need of such a treatment may be a subject who is obese, likely to become obese, overweight, or likely to become overweight. Subjects who are likely to become obese or overweight can be identified, for example, based on family history, genetics, diet, activity level, medication intake, or various combinations thereof.

In other embodiments, ANXA1 peptides of this invention that increase the level and/or activity of a SIRT protein may be administered to subjects suffering from a variety of other diseases and conditions that may be treated or prevented by promoting weight loss in the subject. Such diseases include, for example, high blood pressure, hypertension, high blood cholesterol, dyslipidemia, type 2 diabetes, insulin resistance, glucose intolerance, hyperinsulinemia, coronary heart disease, angina pectoris, congestive heart failure, stroke, gallstones, cholecystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), bladder control problems (such as stress incontinence); uric acid nephrolithiasis; psychological disorders (such as depression, eating disorders, distorted body image, and low self esteem) and the like. Finally, patients with AIDS can develop lipodystrophy or insulin resistance in response to combination therapies for AIDS.

In another embodiment, ANXA1 peptides of this invention that increase the level and/or activity of a SIRT protein may be used for inhibiting adipogenesis or fat cell differentiation, whether in vitro or in vivo. Such methods may be used for treating or preventing or inhibiting obesity.

In other embodiments, ANXA1 peptides of this invention that increase the level and/or activity of a SIRT protein can be used for reducing appetite and/or increasing satiety, thereby causing weight loss or avoidance of weight gain. A subject in need of such a treatment may be a subject who is overweight, obese or a subject likely to become overweight or obese. The method may comprise administering daily or, every other day, or once a week, a dose, e.g., in the form of a pill, to a subject. The dose may be an "appetite reducing dose."

In an exemplary embodiment, ANXA1 peptides of this invention that increase the level and/or activity of a SIRT protein may be administered as a combination therapy for treating or preventing or inhibiting weight gain or obesity. For example, one or more ANXA1 peptides that increase the level and/or activity of a SIRT protein may be administered in combination with one or more anti-obesity agents.

In another embodiment, ANXA1 peptides of this invention that increase the level and/or activity of a SIRT protein can be administered to reduce drug-induced weight gain. For example, an ANXA1 peptide of this invention that increases the level and/or activity of a SIRT protein can be administered as a combination therapy with medications that may stimulate appetite or cause weight gain, in particular, weight gain due to factors other than water retention.

In another aspect, ANXA1 peptides of this invention that increase the level and/or activity of a SIRT protein can be used for treating or preventing a metabolic disorder, such as insulin-resistance, a pre-diabetic state, type II diabetes, and/or complications thereof. Administration of an ANXA1 peptide of this invention that increases the level and/or activity of a SIRT protein can increase insulin sensitivity and/or decrease insulin levels in a subject. A subject in need of such a treatment may be a subject who has insulin resistance or other precursor symptom of type II diabetes, who has type II diabetes, or who is likely to develop any of these conditions. For example, the subject may be a subject having insulin resistance, e.g., having high circulating levels of insulin and/or associated conditions, such as hyperlipidemia, dyslipogenesis, hypercholesterolemia, impaired glucose tolerance, high blood glucose sugar level, other manifestations of syndrome X, hypertension, atherosclerosis and/or lipodystrophy.

In an exemplary embodiment, ANXA1 peptides of this invention that increase the level and/or activity of a SIRT protein may be administered as a combination therapy for treating or preventing a metabolic disorder. For example, one or more ANXA1 peptides that increase the level and/or activity of a SIRT protein may be administered in combination with one or more anti-diabetic agents.

In other aspects, ANXA1 peptides of this invention that increase the level and/or activity of a SIRT protein can be used to treat or prevent a disease or disorder associated with inflammation. ANXA1 peptides that increase the level and/or or activity of a SIRT protein may be administered prior to the onset of, at, or after the initiation of inflammation. When used prophylactically, the ANXA1 peptide can be provided in advance of any inflammatory response or symptom. Administration of the ANXA1 peptide may prevent or attenuate inflammatory responses or symptoms.

In another embodiment, ANXA1 peptides of this invention that increase the level and/or activity of a SIRT protein may be used to treat or prevent allergies and respiratory conditions, including asthma, bronchitis, pulmonary fibrosis, allergic rhinitis, oxygen toxicity, emphysema, chronic bronchitis, acute respiratory distress syndrome, and any chronic obstructive pulmonary disease (COPD). The ANXA1 peptides may be used to treat chronic hepatitis infection, including hepatitis B and hepatitis C.

Additionally, ANXA1 peptides of this invention that increase the level and/or activity of a SIRT protein may be used to treat autoimmune diseases and/or inflammation associated with autoimmune diseases such as arthritis, including rheumatoid arthritis, psoriatic arthritis, and ankylosing spondylitis, as well as organ-tissue autoimmune diseases (e.g., Raynaud's syndrome), ulcerative colitis, Crohn's disease, oral mucositis, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease (also known as autoimmune polyglandular syndrome), and/or Graves disease, in any combination.

In some embodiments, one or more ANXA1 peptides of this invention that increase the level and/or activity of a SIRT protein may be taken alone or in combination with other compounds useful for treating or preventing inflammation.

In another aspect, ANXA1 peptides of this invention that increase the level and/or activity of a SIRT protein may be used for reducing the incidence or severity of flushing and/or hot flashes which are symptoms of a disorder. For instance, the subject method includes the use of ANXA1 peptides of this invention that increase the level and/or activity of a SIRT protein, alone or in combination with other agents, for reducing incidence or severity of flushing and/or hot flashes in cancer patients. In other embodiments, the method provides for the use of ANXA1 peptides of this invention that increase the level and/or activity of a SIRT protein to reduce the incidence or severity of flushing and/or hot flashes in menopausal and post-menopausal woman.

In another aspect, ANXA1 peptides of this invention that increase the level and/or activity of a SIRT protein may be used as a therapy for reducing the incidence or severity of flushing and/or hot flashes which are side-effects of another drug therapy, e.g., drug-induced flushing. In certain embodiments, a method for treating and/or preventing drug-induced flushing comprises administering to a subject in need thereof a formulation comprising at least one flushing inducing compound and at least one ANXA1 peptide of this invention that increases the level and/or activity of a SIRT protein. In other embodiments, a method for treating drug-induced flushing comprises separately administering one or more compounds that induce flushing and one or more ANXA1 peptides of this invention, e.g., wherein the ANXA1 peptide and flushing inducing agent have not been formulated in the same compositions. When using separate formulations, the ANXA1 peptides of this invention may be administered (1) at the same as administration of the flushing inducing agent, (2) intermittently with the flushing inducing agent, (3) staggered relative to administration of the flushing inducing agent, (4) prior to administration of the flushing inducing agent, (5) subsequent to administration of the flushing inducing agent, and (6) various combination thereof. Exemplary flushing inducing agents include, for example, niacin, raloxifene, antidepressants, anti-psychotics, chemotherapeutics, calcium channel blockers, and antibiotics.

In some embodiments, ANXA1 peptides of this invention that increase the level and/or activity of a SIRT protein may be used to reduce flushing side effects of a vasodilator or an antilipemic agent (including anticholesteremic agents and lipotropic agents). In an exemplary embodiment, an ANXA1 peptide of this invention that increases the level and/or activity of a SIRT protein may be used to reduce flushing associated with the administration of niacin.

In another embodiment, the invention provides a method for treating and/or preventing hyperlipidemia with reduced flushing side effects. In another representative embodiment, the method involves the use of an ANXA1 peptide of this invention that increases the level and/or activity of a SIRT protein to reduce flushing side effects of raloxifene. In another representative embodiment, the method involves the use of ANXA1 peptides of this invention that increase the level and/or activity of a SIRT protein to reduce flushing side effects of antidepressants or anti-psychotic agent. For instance, ANXA1 peptides of this invention that increase the level and/or activity of a SIRT protein can be used in conjunction (administered separately or together) with a serotonin reuptake inhibitor, or a 5HT2 receptor antagonist.

In certain embodiments, ANXA1 peptides of this invention that increase the level and/or activity of a SIRT protein may be used as part of a treatment with a serotonin reuptake inhibitor (SR1) to reduce flushing. In still another representative embodiment, ANXA1 peptides of this invention that increase the level and/or activity of a SIRT protein may be used to reduce flushing side effects of chemotherapeutic agents, such as cyclophosphamide and tamoxifen.

In another embodiment, ANXA1 peptides of this invention that increase the level and/or activity of a SIRT protein may be used to reduce flushing side effects of calcium channel blockers, such as amlodipine.

In a further embodiment, ANXA1 peptides of this invention that increase the level and/or activity of a SIRT protein may be used to reduce flushing side effects of antibiotics. For example, ANXA1 peptides that increase the level and/or activity of a SIRT protein can be used in combination with levofloxacin.

One aspect of the present invention is a method for inhibiting, reducing or otherwise treating vision impairment by administering to a patient a therapeutic dosage of an ANXA1 peptide of this invention.

In certain aspects of the invention, the vision impairment is caused by damage to the optic nerve or central nervous system. In particular embodiments, optic nerve damage is caused by high intraocular pressure, such as that created by glaucoma. In other embodiments, optic nerve damage is caused by swelling of the nerve, which can be associated with an infection or an immune (e.g., autoimmune) response such as in optic neuritis.

In certain aspects of the invention, the vision impairment is caused by retinal damage. In particular embodiments, retinal damage is caused by disturbances in blood flow to the eye (e.g., arteriosclerosis, vasculitis). In particular embodiments, retinal damage is caused by disruption of the macula (e.g., exudative or non-exudative macular degeneration).

Exemplary retinal diseases include Exudative Age Related Macular Degeneration, Nonexudative Age Related Macular Degeneration, Retinal Electronic Prosthesis and RPE Transplantation Age Related Macular Degeneration, Acute Multifocal Placoid Pigment Epitheliopathy, Acute Retinal Necrosis, Best Disease, Branch Retinal Artery Occlusion, Branch Retinal Vein Occlusion, Cancer Associated and Related Autoimmune Retinopathies, Central Retinal Artery Occlusion, Central Retinal Vein Occlusion, Central Serous Chorioretinopathy, Eales Disease, Epimacular Membrane, Lattice Degeneration, Macroaneurysm, Diabetic Macular Edema, Irvine-Gass Macular Edema, Macular Hole, Subretinal Neovascular Membranes, Diffuse Unilateral Subacute Neuroretinitis, Nonpseudophakic Cystoid Macular Edema, Presumed Ocular Histoplasmosis Syndrome, Exudative Retinal Detachment, Postoperative Retinal Detachment, Proliferative Retinal Detachment, Rhegmatogenous Retinal Detachment, Tractional Retinal Detachment, Retinitis Pigmentosa, CMV Retinitis, Retinoblastoma, Retinopathy of Prematurity, Birdshot Retinopathy, Background Diabetic Retinopathy, Proliferative Diabetic Retinopathy, Hemoglobinopathies Retinopathy, Purtscher Retinopathy, Valsalva Retinopathy, Juvenile Retinoschisis, Senile Retinoschisis, Terson Syndrome and White Dot Syndromes.

Other exemplary diseases include ocular bacterial infections (e.g., conjunctivitis, keratitis, tuberculosis, syphilis, gonorrhea), viral infections (e.g., Ocular Herpes Simplex Virus, Varicella Zoster Virus, Cytomegalovirus retinitis, Human Immunodeficiency Virus (HIV)) as well as progressive outer retinal necrosis secondary to HIV or other HIV-associated and other immunodeficiency-associated ocular diseases. In addition, ocular diseases include fungal infections (e.g., *Candida* choroiditis, histoplasmosis), protozoal infections (e.g., toxoplasmosis) and others such as ocular toxocariasis and sarcoidosis.

One aspect of the invention is a method for inhibiting, reducing or treating vision impairment in a subject undergoing treatment with a chemotherapeutic drug (e.g., a neurotoxic drug, a drug that raises intraocular pressure such as a steroid), by administering to the subject in need of such treatment a therapeutic dosage of an ANXA1 peptide of this invention.

Another aspect of the invention is a method for inhibiting, reducing or treating vision impairment in a subject undergoing surgery, including ocular or other surgeries performed in the prone position such as spinal cord surgery, by administering to the subject in need of such treatment a therapeutic dosage of an ANXA1 peptide of this invention. Ocular surgeries include cataract, iridotomy and lens replacements.

Another aspect of the invention is the treatment, including inhibition and prophylactic treatment, of age-related ocular diseases including cataracts, dry eye, age-related macular degeneration (AMD), retinal damage and the like, by administering to the subject in need of such treatment a therapeutic dosage of an ANXA1 peptide of this invention.

Another aspect of the invention is the prevention, inhibition or treatment of damage to the eye caused by stress, chemical insult or radiation, by administering to the subject in need of such treatment a therapeutic dosage of an ANXA1 peptide of this invention. Radiation or electromagnetic damage to the eye can include that caused by CRT's or exposure to sunlight or UV.

In one embodiment, a combination drug regimen may include drugs or compounds for the treatment or prevention of ocular disorders or secondary conditions associated with these conditions. Thus, a combination drug regimen may include one or more ANXA1 peptides of this invention and one or more therapeutic agents for the treatment of an ocular disorder.

In one embodiment, an ANXA1 peptide of this invention can be administered in conjunction with a therapy for reducing intraocular pressure. In another embodiment, an ANXA1 peptide of this invention can be administered in conjunction with a therapy for treating and/or preventing glaucoma. In yet another embodiment, an ANXA1 peptide of this invention can be administered in conjunction with a therapy for treating and/or preventing optic neuritis. In one embodiment, an ANXA1 peptide of this invention can be administered in conjunction with a therapy for treating and/or preventing CMV Retinopathy. In another embodiment, an ANXA1 peptide of this invention can be administered in conjunction with a therapy for treating and/or preventing multiple sclerosis.

In certain embodiments, the invention provides methods for treating diseases or disorders that would benefit from increased mitochondrial activity. The methods involve administering to a subject in need thereof a therapeutically effective amount of an ANXA1 peptide of this invention. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, diseases and disorders that would benefit from increased mitochondrial activity include diseases or disorders associated with mitochondrial dysfunction.

Diseases and disorders associated with mitochondrial dysfunction include diseases and disorders in which deficits in mitochondrial respiratory chain activity contribute to the development of pathophysiology of such diseases or disorders in a mammal. Diseases or disorders that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis.

In certain embodiments, the invention provides methods for treating a disease or disorder that would benefit from increased mitochondrial activity that involves administering to a subject in need thereof one or more ANXA1 peptide of this invention in combination with another therapeutic agent such as, for example, an agent useful for treating mitochondrial dysfunction or an agent useful for reducing a symptom associated with a disease or disorder involving mitochondrial dysfunction.

In exemplary embodiments, the invention provides methods for treating diseases or disorders that would benefit from increased mitochondrial activity by administering to a subject a therapeutically effective amount of an ANXA1 peptide of this invention. Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, chronic pain, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and/or mitochondrial deregulation, in any combination.

Muscular dystrophy refers to a collection of diseases and disorders involving deterioration of neuromuscular structure and function, often resulting in atrophy of skeletal muscle and myocardial dysfunction, such as Duchenne muscular dystrophy. In certain embodiments, an ANXA1 peptide of this invention may be used for reducing the rate of decline in muscular functional capacities and for improving muscular functional status in patients with muscular dystrophy.

In certain embodiments, an ANXA1 peptide of this invention may be useful for treatment of mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal).

In certain embodiments, an ANXA1 peptide of this invention may be useful for treating patients suffering from toxic damage to mitochondria, such as toxic damage due to calcium accumulation, excitotoxicity, nitric oxide exposure, drug induced toxic damage, and/or hypoxia.

In certain embodiments, an ANXA1 peptide of this invention may be useful for treating diseases or disorders associated with mitochondrial deregulation.

In other embodiments, the invention provides methods for enhancing muscle performance by administering a therapeutically effective amount of an ANXA1 peptide of this invention. For example, an ANXA1 peptide of this invention may be useful for improving physical endurance (e.g., ability to perform a physical task such as exercise, physical labor, sports activities, etc), inhibiting or retarding physical fatigues, enhancing blood oxygen levels, enhancing energy in healthy individuals, enhance working capacity and endurance, reducing muscle fatigue, reducing stress, enhancing cardiac and cardiovascular function, improving sexual ability, increasing muscle ATP levels, and/or reducing lactic acid in blood. In certain embodiments, the methods involve administering an amount of an ANXA1 peptide of this invention that increase mitochondrial activity, increase mitochondrial biogenesis, and/or increase mitochondrial mass.

Sports performance refers to the ability of the athlete's muscles to perform when participating in sports activities. Enhanced sports performance, strength, speed and endurance are measured by an increase in muscular contraction strength, increase in amplitude of muscle contraction, shortening of muscle reaction time between stimulation and contraction. Athlete refers to an individual who participates in sports at any level and who seeks to achieve an improved level of strength, speed and endurance in their performance, such as, for example, body builders, bicyclists, long distance runners, short distance runners, etc. Enhanced sports performance in manifested by the ability to overcome muscle fatigue, ability to maintain activity for longer periods of time, and have a more effective workout.

It is contemplated that the methods of the present invention will also be effective in the treatment of muscle related pathological conditions, including acute sarcopenia, for example, muscle atrophy and/or cachexia associated with burns, bed rest, limb immobilization, or major thoracic, abdominal, and/or orthopedic surgery.

In certain embodiments, the invention provides dietary compositions comprising an ANXA1 peptide of this invention, a method for preparation, and a method of using the compositions for, e.g., improvement of sports and/or athletic and/or physical performance. Accordingly, provided are therapeutic compositions, foods and beverages that have actions of improving physical endurance and/or inhibiting physical fatigue in a subject in need thereof, including for example, subjects involved in broadly-defined exercises including sports requiring endurance and/or labor requiring repeated muscle exertions. Such dietary compositions may additional comprise electrolytes, caffeine, vitamins, carbohydrates, etc., in any combination.

ANXA1 peptides of this invention that increase the level and/or activity of a SIRT protein can be used for treating and/or preventing or inhibiting diseases and/or disorders caused by a viral infection (such as infection by influenza, herpes or papilloma virus) or as an antifungal agent. In certain embodiments, an ANXA1 peptide of this invention that increases the level and/or activity of a SIRT protein may be administered as part of a combination drug therapy with one or more therapeutic agent for the treatment of viral-associated diseases and disorders. In another embodiment, an ANXA1 peptide of this invention that increases the level and/or activity of a SIRT protein may be administered as part of a combination drug therapy with one or more anti-fungal agent.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells. For example, an ANXA1 peptide of this invention may be administered to farm animals to increase their lifespan and/or improve their ability to withstand farming conditions longer.

ANXA1 peptides of this invention that increase the level and/or activity of a SIRT protein may also be used to increase lifespan, stress resistance, and resistance to apoptosis in plants. In one embodiment, an ANXA1 peptide can be applied to plants, e.g., on a periodic basis, or to fungi. In another embodiment, plants can be genetically modified to produce an ANXA1 peptide of this invention. In another embodiment, plants and fruits are treated with an ANXA1 peptide of this invention prior to picking and shipping to increase resistance to damage during shipping. Plant seeds may also be contacted with an ANXA1 peptide of this invention, e.g., to preserve them.

In other embodiments, an ANXA1 peptide of this invention that increases the level and/or activity of a SIRT protein may be used for modulating lifespan in yeast cells. Situations in which it may be desirable to extend the lifespan of yeast cells include any process in which yeast is used, e.g., the making of beer, yogurt, and bakery items, e.g., bread. Use of yeast having an extended lifespan can result in using less yeast or in having the yeast be active for longer periods of time. Yeast or other mammalian cells used for recombinantly producing proteins may also be treated as described herein.

An ANXA1 peptide of this invention that increases the level and/or activity of a SIRT protein can also be used to increase lifespan, stress resistance and resistance to apoptosis in insects. In this embodiment, an ANXA1 peptide of this invention would be applied to useful insects, e.g., bees and other insects that are involved in pollination of plants. In a specific embodiment, an ANXA1 peptide of this invention would be applied to bees involved in the production of honey. Generally, the methods described herein may be applied to any organism, e.g., eukaryote, which may have commercial importance. For example, an ANXA1 peptide of this invention can be applied to fish (aquaculture) and birds (e.g., chicken and fowl).

Higher doses of an ANXA1 peptide of this invention that increases the level and/or activity of a SIRT protein can be used as a pesticide by interfering with the regulation of silenced genes and the regulation of apoptosis during development. In this embodiment, an ANXA1 peptide of this invention can be applied to plants using a method known in the art that ensures the ANXA1 peptide of this invention is bio-available to insect larvae, and not to plants.

In view of the link between reproduction and longevity, an ANXA1 peptide of this invention that increases the level and/or activity of a SIRT protein can be applied to affect the reproduction of organisms such as insects, animals and microorganisms.

The present invention also relates to a cosmetic or pharmaceutical composition, comprising an ANXA1 peptide of this invention used alone or in combination with at least one other active agent, in a physiologically acceptable medium.

The invention also relates to the utilization of an ANXA1 peptide of this invention as an active agent in a cosmetic composition. The invention further relates to the utilization of a cosmetic composition to prevent and/or repair DNA degradation, improve telomere maintenance and reduce cellular senescence. Also, the invention applies to a cosmetic treatment process intended to prevent and/or treat the cutaneous signs of aging and photo aging, according to which an effective amount of an ANXA1 peptide of this invention, or a composition containing an ANXA1 peptide of this invention, is applied to the area(s) to be treated.

Aging corresponds to the set of physiological processes that modify the structure and functions of the organism according to the time and stresses undergone. Intrinsic aging due to genetic factors and biochemical modifications that take place during states of fatigue and stress and hormonal changes such as pregnancy, etc., may be distinguished from extrinsic aging due to environmental factors to which the organism is subjected throughout its life, such as pollution, sunlight, disease, lifestyle, etc. Aging is a slow and progressive process that affects all cells and organs. Thus this applies to the skin, which constitutes a barrier between the external environment and the inner medium and protects the organism against external stresses. During aging, the appearance of the skin changes and thus wrinkles and fine lines, hyper- or hypopigmentation spots, dryness and even dehydration of the skin, thinning of the epidermis, elastosis, etc., may appear.

Cellular senescence phenomena are accelerated by oxidative damage, particularly in areas of the body where the skin is exposed to the sun; photo aging is then superimposed on intrinsic aging. Oxidative damage is promoted by various agents, both endogenous (metabolism, inflammation, redox cycles) and exogenic, such as UV radiation and ionizing radiation, tobacco abuse and various molecules supplied by the diet (toxic metals, alcohol). Damage caused by oxidative stress also reaches the DNA and lipids and proteins. At the DNA level, oxidative stress causes many structural modifications (mutations, cleavage, covalent protein cross-links). Oxidized bases, such as 8-oxo-guanine, increase with age and may reach up to 10,000 bases per day and per cell.

The ANXA1 peptide or peptides of this invention can be formulated to preserve and/or increase the stability and/or bioavailability of the ANXA1 peptide or peptides. Nonlimiting examples of such formulations include adding or linking or combining the peptide or peptides of this invention with a polyalkylene glycol (e.g., polyethylene glycol (PEG)) and or an inhibitor of proteolytic activity.

Pharmaceutical compositions of this invention may be prepared as medicaments to be administered in any method suitable for the subject's condition, for example, orally, parenterally (including subcutaneous, intramuscular, and intravenous), rectally, transdermally, buccally, or nasally, or may be delivered directly to the heart by injection and/or catheter, or may be delivered to the eye as a liquid solution.

Suitable forms for oral administration include, but are not limited to, tablets, powders, compressed or coated pills, dragees, sachets, hard or gelatin capsules, sub-lingual tablets, syrups, and suspensions. Suitable forms of parenteral administration include, but are not limited to, an aqueous or non-aqueous solution or emulsion. Suitable forms for rectal administration, include, but are not limited to, suppositories with hydrophilic or hydrophobic vehicles. For topical administration, suitable forms include, but are not limited to, suitable transdermal delivery systems known in the art, such as patches, and for nasal delivery, suitable forms include, but are not limited to, aerosol and nebulized delivery systems known in the art.

In addition to the ANXA1 peptides provided herein, pharmaceutical compositions of the present invention may contain one or more excipients or adjuvants. Selection of excipients and/or adjuvants and the amounts to use may be readily determined by the formulation scientist upon experience and consideration of standard procedures and reference works in the field.

Excipients such as diluents increase the bulk of a solid pharmaceutical composition, and may make a pharmaceutical dosage form containing the composition easier for the patient and care giver to handle. Diluents for solid compositions include, but are not limited to, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, or talc.

Solid pharmaceutical compositions that are compacted into a dosage form, such as a tablet, may include, but are not limited to, excipients whose functions include, but are not limited to, helping to bind the active ingredient and other excipients together after compression, such as binders. Binders for solid pharmaceutical compositions include, but are not limited to, acacia, alginic acid, carbomer (e.g., CARBOPOL®), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate, or starch.

The dissolution rate of a compacted solid pharmaceutical composition in the subject's stomach may be increased by the addition of a disintegrant to the composition. Excipients which function as disintegrants include, but are not limited to, alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®), or starch.

Glidants can be added to improve the flowability of a non-compacted solid composition and to improve the accuracy of dosing. Excipients that may function as glidants include, but are not limited to, colloidal silicon dioxide, magnesium trisilicate, powdered cellulose, starch, talc, or tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Excipients that function as lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, or zinc stearate.

Flavoring agents and flavor enhancers make the dosage form more palatable to the patient. Common flavoring agents and flavor enhancers for pharmaceutical products that may be included in the composition of the invention include, but are not limited to, maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the active ingredient and any other solid excipients are suspended in a liquid carrier such as water, vegetable oil, alcohol, polyethylene glycol, propylene glycol, or glycerin. As used herein, "active ingredient" means ANXA1 peptides described herein.

Liquid pharmaceutical compositions may contain emulsifying agents to disperse uniformly throughout the composition an active ingredient or other excipient that is not soluble in the liquid carrier. Emulsifying agents that may be useful in liquid compositions of the invention include, but are not limited to, gelatin, egg yolk, casein, cholesterol, acacia, tragacanth, chondrus, pectin, methyl cellulose, carbomer, cetostearyl alcohol, or cetyl alcohol.

Liquid pharmaceutical compositions of the present invention may also contain a viscosity enhancing agent to improve the mouth-feel of the product and/or coat the lining of the gastrointestinal tract. Such agents include, but are not limited to, acacia, alginic acid, bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, or xanthan gum.

Sweetening agents such as sorbitol, saccharin, sodium saccharin, sucrose, aspartame, fructose, mannitol, or invert sugar may be added to improve the taste.

Preservatives and chelating agents such as alcohol, sodium benzoate, butylated hydroxy toluene, butylated hydroxyanisole, or ethylenediamine tetraacetic acid may be added at levels safe for ingestion to improve storage stability.

According to the invention, a liquid composition may also contain a buffer such as gluconic acid, lactic acid, citric acid or acetic acid, sodium gluconate, sodium lactate, sodium citrate, or sodium acetate.

An amount of an ANAXA1 peptide adequate to accomplish therapeutic or prophylactic treatment as described herein is defined as a therapeutically or prophylactically-effective amount or as an effective amount. In both prophylactic and therapeutic regimens, ANXA1 peptides of the present invention can be administered in several dosages until a desired effect has been achieved.

Effective doses of the compositions of the present invention, for the treatment of the above described conditions vary depending upon many different factors, including means or mode of administration, target site, physiological state of the subject, whether the subject is human or an animal, other medications administered, and whether treatment is prophylactic or therapeutic. Usually, the subject is a human but nonhuman mammals including transgenic mammals can also be treated. Treatment dosages can be titrated to optimize safety and efficacy. Generally, an effective amount of the agents described above will be determined by the age, weight and condition or severity of disease of the subject.

The amount of ANXA1 peptide depends on whether additional active and/or inactive compounds, such as pharmaceutical carriers, are also administered, with higher dosages being required in the absence of additional compounds. The amount of an ANXA1 peptide for administration can be from about 1 µg to about 500 µg per patient and in some embodiments can be from about 5 µg to about 500 µg per administration for human administration. In particular embodiments, a higher dose of about 1-2 mg per administration can be used. Typically about 5, 10, 20, 50 or 100 µg is used for each human administration.

Generally, dosing may be one or more times daily, or less frequently, such as once a day, once a week, once a month, once a year, once in a decade, etc. and may be in conjunction with other compositions as described herein. In certain embodiments, the dosage is greater than about 1 µg/subject and usually greater than about 10 µg/subject if additional compounds are also administered, and greater than about 10 µg/subject and usually greater than about 100 µg/subject in the absence of additional compounds, such as a pharmaceutical carrier. It should be noted that the present invention is not limited to the dosages recited herein.

The dosage and frequency of administration can vary depending on whether the treatment is prophylactic or therapeutic. In prophylactic applications, a relatively low dosage can be administered at relatively infrequent intervals over a long period of time. Some patients may continue to receive treatment for the rest of their lives. In therapeutic applications, a relatively high dosage at relatively short intervals is sometimes required until severity of the injury is reduced or terminated, and preferably until the subject shows partial or complete amelioration of symptoms of injury. Thereafter, the subject can be administered a prophylactic regimen.

The aforementioned embodiments are not exclusive and may be combined in whole or in part. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

The present invention is explained in greater detail in the following non-limiting examples.

EXAMPLES

Example 1. Annexin-A1 Biomimetic Peptide Attenuates Myocardial Ischemia-Reperfusion Injury Via Increased Sirtuin-3

Cardioprotection—an Unmet Clinical Need:

Cardiovascular events, such as myocardial infarction and acute heart failure are the predominant causes of perioperative morbidity and mortality in patients after surgery and occur at high frequency, especially in elderly patients with coronary artery disease and left ventricular dysfunction undergoing major surgery. The demographics of patients undergoing surgery show an aging population and increased co-morbidities in the US, and now notably in developing nations. Thus, there is an increasing worldwide need for proven, effective therapies for prevention or perioperative cardiovascular morbidity and mortality in high-risk populations. Cardiac operations, heart transplantation, and coronary angioplasty are associated with obligatory myocardial ischemia and reperfusion (IR). While cardiopulmonary bypass (CPB) and cardioplegic arrest (CA) or deep hypothermic circulatory arrest (DHCA) remain the most popular strategies for clinical intervention during open-heart surgery, both can directly or indirectly trigger inflammatory responses, metabolic abnormalities and mitochondrial dysfunction that largely contribute to perioperative myocardial infarction (PMI) after cardiac surgery, the incidence of which remains as high as 19%. There is however a fundamental gap in understanding how aging increases cardiac vulnerability to surgical stress and ischemia-reperfusion (IR) injury, particularly in patients with ventricular dysfunction. A number of observations draw a link among loss of mitochondrial function, aging, and impaired recovery from IR injury of aged hearts. Mitochondria play important roles in mediating apoptosis and necrosis following myocardial ischemia-reperfusion (IR). Taken together, these synergistic components of the inflammatory response and mitochondrial dysfunction exacerbate myocardial injury, ultimately resulting in myocardial cell death and deterioration of cardiac function. Accordingly, modulating the inflammatory response or preventing mitochondrial dysfunction, have been recognized as important cardioprotective targets in the context of PMI. Translation of experimental cardioprotective strategies into clinical therapy remains an ongoing challenge, as evidenced by recent failures of paxelizumab, MC-1, and acadesine in phase-III RCTs, in part because preclinical studies use animal models that do not adequately approximate the cardiac surgical setting, lack of emphasis efficacy, and focus on imprecisely defined mechanisms.

Annexin-A1 (ANXA1) is an endogenous glucocorticoid-regulated protein with potent inflammation resolving properties, previously implicated in attenuating myocardial ischemia-reperfusion (IR) injury via neutrophil-mediated mechanisms. More recently, ANXA1 has emerged as a key effector molecule in the resolution of inflammation, effects mediated by the formyl peptide receptor (FPR) family. Although several studies have shown that an N-terminal peptide mimetic of ANXA1 (Ac2-26) inhibits neutrophil dependent myocardial necrosis in rat coronary ligation models, and improves post-ischemic recovery of ventricular contractile function ex vivo, the role of ANXA1 modulation in cardioprotection following the complex and profound global IR injury associated with cardiac surgery has not been reported. Furthermore, we have recently found that ANXA1 inflammation resolving and cardioprotection are in part mediated through regulation of protein deacetylation. Sirtuins, a family of $NAD^+$-dependent protein deacetylases, have emerged as important regulators of aging, chronic inflammation and cancer, mediating adaptive responses to a variety of stressors including caloric restriction and metabolic stress, and more recently with cardioprotective roles following IR. Recent studies have identified targets of the major mitochondrial deacetylase sirtuin3 (SIRT3) to include key metabolic enzymes involved in increasing acetate recycling, fatty acid oxidation (FAO), mitochondrial oxidative phosphorylation and urea cycle, suggesting its role in promoting energy production from sources that detour from glucose utilization.

Studies were conducted to determine whether Annexin A1 biomimetic short peptide (ANXA1sp) attenuates myocardial IR injury in vitro and in vivo through differential upregulation of SIRT3 and downstream signaling pathways leading to preservation of mitochondrial function.

ANXA1 Biomimetic Peptide.

The ANXA1 tripeptide (ANXA1sp or Ac-$Q^{10}A^{11}W^{12}$; Ac: acetyl) derived from N-terminal domain of human ANXA1 sequence and a scrambled peptide (scrPEP or Ac-$W^{10}Q^{11}A^{12}$; Ac: acetyl) served as a negative control were synthesized by GenScript (Piscataway, N.J.), with >98% purity reached by HPLC with Alltima™ C18 column (4.6×250 mm) and the observed M.W. 445.25 (based on the data from mass spectrum provided by GenScript). ANXA1sp or scrPEP was first resuspended in DMSO and then dissolved in normal saline (to a concentration of 1 mg/ml) for in vivo administration or diluted with culture medium to the final concentrations for in vitro experiments.

In a series of experiments outlined below, ANXA1sp was administered to adult rat cardiomyocytes subject to simulated IR, as well as rats undergoing cardiopulmonary bypass with cardioplegic arrest (CA) or deep hypothermic circulatory arrest (DHCA). Cardioprotective efficacy endpoints and mechanisms assessed at 3, 6, and 24 h post-reoxygenation (ARVC) and post-reperfusion (rat) include markers of myonecrosis and apoptosis, SIRT3 expression and activity and effects on known SIRT3 target proteins. ANXA1sp resulted in marked cardioprotective effects in vitro and in vivo, and significantly increased SIRT3 expression and activity in the cardiomyocytes and the myocardium by increasing expression of mitochondrial matrix peptidase (MPP). Animals treated with ANXA1sp showed significantly increased expression of MnSOD and P-AMPK in the myocardium, as well as significantly reduced myocardial necrosis, apoptosis and preserved ventricular contractile function. Details of the experimental protocols and results follow.

Simulated IR in Adult Rat Ventricular Cardiomyocytes (ARVCs).

Following standard isolation and culture protocols, ARVCs were exposed to ANXA1sp (5, 10, 30, 60 µM) for 1 h, subjected to 2 h of oxygen glucose deprivation (OGD), followed by reoxygenation for 3, 6, or 24 h (FIG. 1). A scrambled peptide and dexamethasone (DEX) were used as negative and positive controls, respectively. ARVC injury was determined at the end of reoxygenation as levels of cardiac Troponin I (cTnI) in the culture medium using high-sensitivity ELISA (Life Diagnostics), viability using cell morphology and Trypan blue exclusion, and apoptosis using a Cell Death ELISA (Roche). Schematics of the ANXA1sp dose-finding and time-course in vitro experiments are presented in FIG. 1.

Isolation and Culture of Adult Rat Ventricular Cardiomyocytes (ARVCs).

ARVCs were isolated from adult (12-15 weeks old) male Sprague-Dawley (SD) rats using a commercial isolation kit (Cellutron, Cat. #AC-7031), according to the manufacturer's protocol. Briefly, male Sprague-Dawley (SD) rats (300-350 g) were anesthetized with 2% isoflurane in oxygen in a plastic box. Ice-cold WB buffer (5 ml) was injected in both ventricles using a 26-gauge needle to arrest the heart and wash out blood. The heart was then quickly removed, carefully cannulated onto the Langendorff perfusion apparatus, and retrogradely perfused with 40 ml B1 buffer at the flow rate of 5 ml/min. The heart was then perfused in a recirculating mode with 50 ml B2 buffer. After 10 min, 100 µl of SB solution was quickly added in the B2 flow through and mixed well. The heart was continually perfused for 10 min. Additional 100 µl SB was added in the B2-SB flow through and continued to perfuse the heart for 15 min. The heart was removed from the apparatus, and the ventricles were separated below atrioventricular junction and cut into several sections in 24 ml of recirculated flow through. The ventricles were agitated in a shaking bath (37° C.) at a rate of 100 rpm for 15 min to release rod-shaped cardiomyocytes. The ventricles were slightly and gently triturated with the transfer pipette from which the tip was broken off and the sharp edges were softened by flame melting. The myocytes were filtered through nylon mesh (250 μM) and allowed to settle by gravity for 2 min. After centrifugation at 500 g for 3 min at room temperature, the cell pellet was resuspended in 10 ml of B3 buffer. After the myocytes were pelleted by gravity for 13 min in the 20 ml of 6.5% BSA in B3 buffer, the myocytes was resuspended in 12 ml of AS Medium (Cellutron Cat#: M-8033). Myocytes were plated in culture dishes pre-coated with laminin (Invitrogen Cat#: 23017-015). Two hours after plating, cells were washed with serum free AW medium (Cellutron Cat#: M-8034), and non-adhering cells were removed from the culturing system. Myocytes were incubated with AW medium in a 37° C. and 5% $CO_2$ growth chamber overnight.

ARVC Model of Simulated IR.

After 24 h incubation, ARVCs were pre-treated with known concentrations of ANXA1sp or scrPEP in growth medium for 1 h, and subjected to 2 h oxygen-glucose-deprivation (OGD: DMEM no glucose, 85% N2/10% H2/5% CO2) in a OGD station chamber/Anaerobic System (Farma Scientific), followed by reoxygenation with 10 μM ANXA1sp or scrPEP in growth medium for 3, 6, and 24 h in a 37° C. and 5% $CO_2$ growth chamber, respectively.

Western Blot.

Proteins were separated by electrophoresis on SDS-PAGE and then transferred onto PVDF-Plus membrane (Millipore). After being blocked with 5% milk, the immunoblots were probed with appropriate antibodies to SIRT3 (Cell Signaling or Abcam), MPP (Santa Cruz), MnSOD, P-AMPK, COXIV, GAPDH (Cell Signaling), and caspase-3 (Cell Signaling, MA) overnight at 4° C. followed by incubation with the corresponding secondary antibodies at room temperature for 1 h. The blots were visualized with the SuperSignal West Dura Extended Duration Substrate (Thermo Scientific) by a gel imaging system (Alpha Innotech).

Immunostaining and Confocal Microscopy.

Confocal studies were performed as described previously. MitoTraker Deep Red FM (Invitrogen) was added into culture medium to make the final concentration of 0.4 μM and incubated at 37° C. for 45 min. After being washed, fixed, permeabilized, and blocked, rabbit monoclonal IgG anti-SIRT3 (Abcam) was added at 4° C. for overnight. Cells were subsequently incubated with Alexa-488 conjugated goat anti-rabbit IgG (Molecular Probes) for 1 h at RT. Images were acquired with a confocal microscope (Zeiss Invert 510 Microscope).

Annexin-A1 Tripeptide Exerts Cytoprotective Effects in ARVC Following Hypoxia-Reoxygenation.

ANXA1sp but not a scrambled peptide significantly reduced Troponin I release from cardiomyocytes following 2 h OGD and 6 h reoxygenation, over a wide range of concentrations (5, 10, 30, and 60 μM), with a maximal effect seen at 10 μM ($P<0.01$, FIG. 1C). A time course analysis revealed that ANXA1sp (10 μM) consistently reduces ARVC injury at both 6 h and 24 h post hypoxia/reoxygenation ($P<0.01$, FIG. 1D). Similar effects were evident on ARVC viability, based on cell morphology (% rod-shaped cardiomyocytes, FIG. 1F) and apoptosis assays ($P<0.01$, FIG. 1E).

ANXA1sp Promotes Survival of Cultured ARVCs after OGD/Reoxygenation by Increased/Activated Mitochondrial SIRT3.

Figure 2:
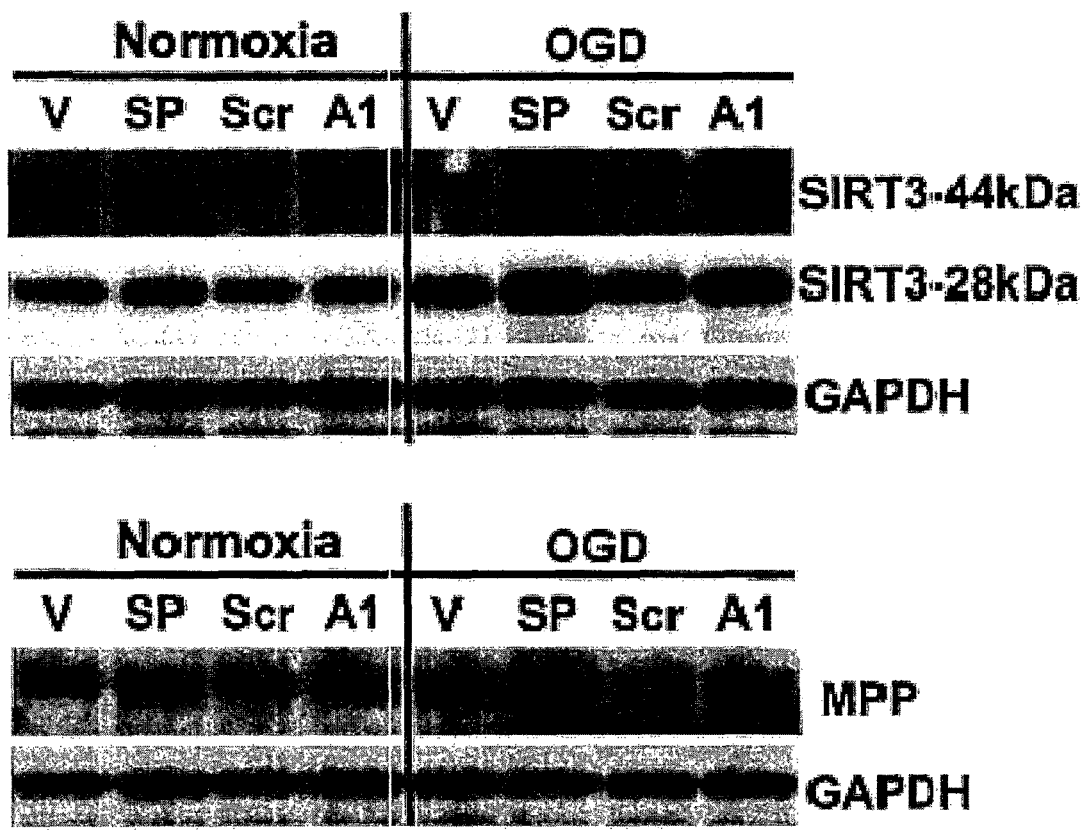
FIG. 2. ANXA1sp increases expression of active SIRT3 (28-kD isoform) and mitochondrial matrix processing peptidase (MPP) in cultured adult rat cardiomyocytes that underwent simulated ischemia-reperfusion in vitro. ARVCs were incubated with ANXA1sp for 1 hour and subjected to 2 hours OGD followed by 3 hours reoxygenation (B), or kept under normoxic conditions (A). Control treatments include vehicle (V), scramble peptide (Scr), and Annexin A1 full-length protein (A1). Expression of SIRT3 (both 44-kD and 28-kD isoforms), as well as mitochondrial matrix processing peptidase (MPP) were determined by Western blot in whole cell lysates (anti-SIRT3 antibody, Abcam, cat# ab56214). ARVC, adult rat ventricular cardiomyocte; OGD, oxygen-glucose deprivation; V, vehicle; SP, ANXA1sp; Scr, scrambled peptide; A1, Annexin A1 full-length protein. GAPDH used as loading control.

Functional relevance and regulatory pathways associated with SIRT3-mediated deacetylation of proteins were analyzed in an in vitro model of simulated IR, i.e., cultured adult rat ventricular cardiomyocytes (ARVCs) exposed to oxygen-glucose deprivation (OGD) and then reoxygenation. This allows for the identification of the proteins that play roles in cell survival, so that their impact in surgical IR can be measured. These studies also provide the basis for determining the extent to which controlled manipulation of post-translational lysine deacetylation of proteins is cardioprotective after IR. These studies have revealed that during simulated IR stress (by OGD), SIRT3 (28-kDa) robustly increased in cell lysates from cultured ARVCs (FIG. 2, upper panel; V—Vehicle, SP—ANXA1sp). In addition, ANXA1sp (SP) but not scrambled peptide (Scr) significantly increased SIRT3 in both full-length and short form proteins after OGD/reoxygenation (FIG. 2, upper panel). ANXA1 (A1, 0.6 μg/ml) treated-ARVCs were used as a positive control. Furthermore, it was found that ANXA1sp (SP) but not scrPEP (Scr) increased mitochondrial matrix processing peptidase (MPP) (FIG. 2, lower panel).

ANXA1sp Increased Mitochondrial SIRT3.

Figure 3:
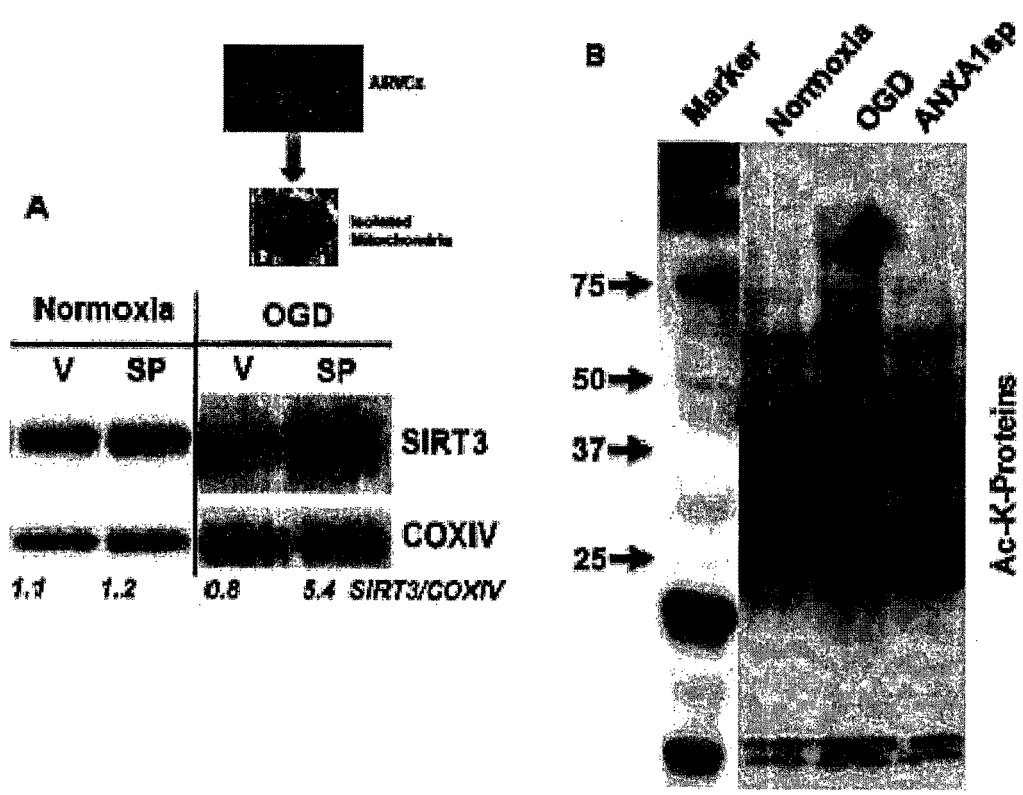
FIG. 3. ANXA1sp increases expression of active SIRT3 (28-kD isoform) in cardiac mitochondria isolated from cultured adult rat cardiomyocytes that underwent simulated ischemia-reperfusion in vitro (panel A). OGD, oxygen-glucose deprivation; V, vehicle control treatment; COXIV used as loading control. Simulated ischemia-reperfusion (OGD) resulted in increased mitochondrial protein lysine-acetylation compared with normoxia, which was reversed by ANXA1sp (panel B).

ANXA1sp treatment increased SIRT3 expression in isolated mitochondria from ARVCs subjected to OGD (FIG. 3). A confocal microscopy study further showed that SIRT3 was significantly increased in mitochondria of cultured ARVCs treated with ANXA1sp, but not scrambled peptide (scrPEP). It was also found that SIRT3 locates in nuclei, and perhaps in cytoplasm as well (FIG. 3, panel A). We confirmed the expected predominant mitochondrial localization of increased SIRT3 expression/activity using confocal microscopy (colocalization of SIRT3 with MitoTracker in ANXA1sp treated ARVCs subjected to OGD/reoxygenation, FIG. 4).

In Vitro Cytoprotective Effects of ANXA1sp.

Figure 19:
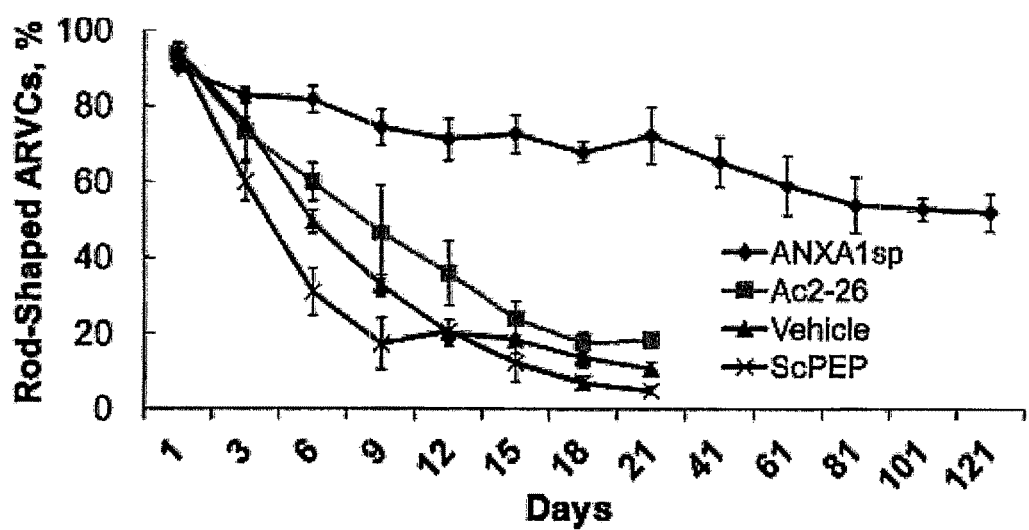
FIG. 19. ANXA1sp has no significant in vitro cytotoxicity and increases lifespan of adult ventricular cardiomyocytes. Cultured ARVCs were incubated with 800 μM ANXA1sp, a commercially available ANXA1 peptide (Ac2-26), scrambled peptide (scrPEP), or vehicle. Media and peptides were changed every three days. Cell viability was determined by cell counts: rod-shaped ARVCs/total ARVCs counted×100%; ARVCs, adult rat ventricular cardiomyocytes.

ARVC cells were exposed to repeat high concentrations (800 μM—20 times higher than the proposed therapeutic concentration) of either ANXA1sp (3mer), a scrambled peptide (scrPEP, 3mer) or a commercial peptide Ac2-26 (25mer), with culture media and agents changed every 3 days, and cell viability was determined by cell counts of rod-shaped cardiomyocytes (%=number of rod-shaped cells/total cells×100). It was found that >50% of ARVCs treated with ANXA1sp but not scrPEP keep their rod-shape morphology for more than 120 days, 5 and 10 times longer than those treated with Ac2-26 and untreated cells, respectively (FIG. 19).

To complement the in vitro findings, further in vivo experiments have also been conducted using well-characterized rodent experimental models of cardiopulmonary bypass (CPB) with global myocardial IR by cardioplegic arrest (CA) and deep hypothermic circulatory arrest (DHCA), which are described herein.

Rat Model of Cardiopulmonary Bypass with Cardioplegic Arrest (CPB/CA) or Deep Hypothermic Circulatory Arrest (DHCA).

Male Sprague-Dawley rats (12-15 weeks old) were randomly assigned to three groups: CA, CA+ANXA1sp, or CA+scrambled peptide. Rats were anesthetized with isoflurane and intubated, and then vascular access was gained via the tail artery (arterial inflow), jugular vein (venous outflow), right common carotid artery (endoaortic balloon), and inferior epigastric artery and vein for invasive blood pressure monitoring and IV access (FIG. 10A). Heparin was administered before initiation of mildly hypothermic CPB (33° C.). A balloon catheter was placed in the ascending aorta and positioned approximately 3-4 mm proximal to the aortic valve under echocardiographic guidance, and inflated before cardioplegia was administered distal to the balloon and into the coronary vasculature. Heart function was monitored with electrocardiography (EKG) and echocardiography, and additional cardioplegia was administered as needed to maintain cardiac arrest. Acid base status, gas exchange, electrolyte, hemoglobin and glucose concentrations were measured with serial arterial blood gases (GEM Premier 3000).

All animals underwent 75 minutes of moderate hypothermic (33° C.) CPB with 45 minutes of cardiac arrest using blood cardioplegia, followed by reperfusion for 3 h, 6 h or 24 h (n=8/group and time point). Treated animals received ANXA1sp (3 mg/kg total) before (iv), during (with cardioplegia), and after CPB (iv), whereas CA animals received an equal volume of vehicle (1% DMSO in saline (FIG. 10B). At the end of the ischemic period the aortic balloon was deflated and cardioplegia was allowed to wash out of the heart. The animal was weaned off the heart-lung machine as tolerated; epinephrine, phenylephrine, and lidocaine were administered as needed to maintain appropriate perfusion and blood pressure. Animals were recovered for a period of 3, 6, or 24 hours of reperfusion (n=8/group and time point), final endpoint measurements obtained, then sacrificed via exsanguination. Immediately following sacrifice, left ventricular myocardial samples were preserved for study.

Figure 10:
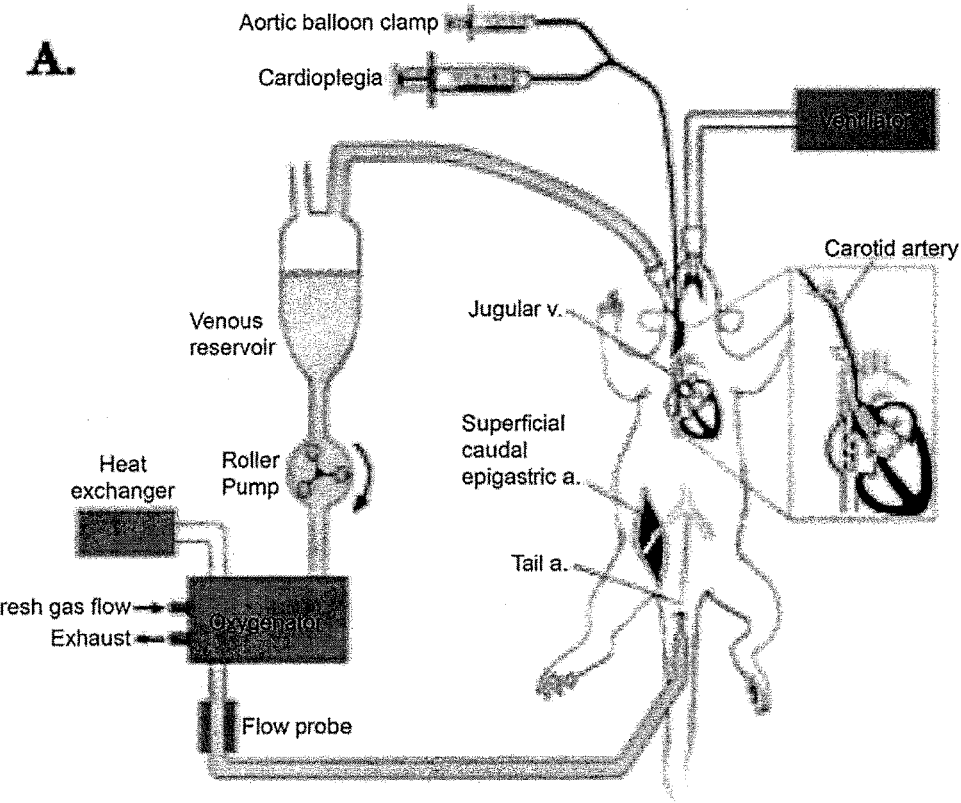
FIG. 10. Cardioprotective effects of ANXA1sp were tested in vivo, using rat models of cardiopulmonary bypass with cardioplegic arrest (CA) and deep hypothermic circulatory arrest (DHCA). A diagram of surgical, perfusion and cardioplegic arrest preparation (panel A), and schematics of experimental protocols for CA (panel B) and DHCA (panel C) are presented.
Figure 10:
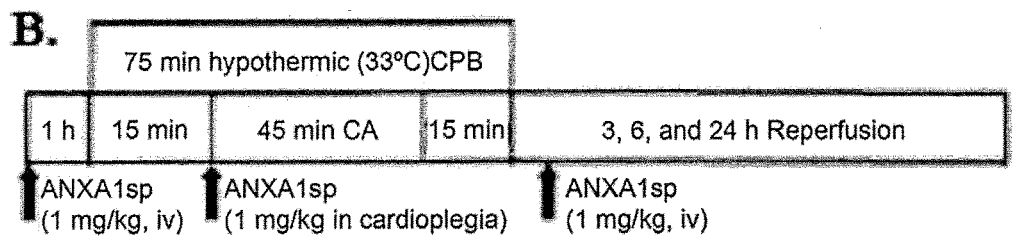
Figure 10:
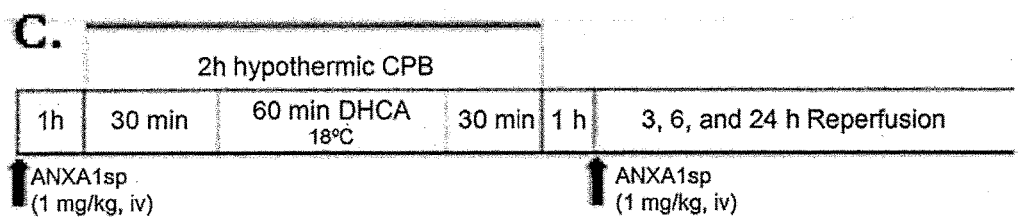

Separate groups of animals underwent 60 minutes of DHCA (18° C.) with a similar treatment design, with animals randomly assigned to sham, CPB/DHCA (Vehicle), DHCA+ANXA1sp (ANXA1sp), or DHCA+scrambled peptide (scrPEP). All rats were subjected to 60 minutes DHCA at 18° C. and received either vehicle (1% DMSO saline), ANXA1sp (total 2 mg/kg), or scrPEP (total 2 mg/kg) iv 1 h before CPB and 1 h after reperfusion (FIG. 10C). Sham operated animals were only cannulated/without CPB/DHCA as baseline control. At 3, 6, and 24 h of post-perfusion, heart and serum samples were harvested. Blood samples were collected and stored at −80° C. until analysis. A small portion of heart tissue from each animal was immediately fixed in 10% buffered formalin, embedded in paraffin, and sectioned for immunostaining, confocal colocalization microscopy, and apoptotic TUNEL staining. Myocardial whole-tissue lysates were obtained at the end of each experiment according to the manufacturer's protocol (Affymetrix). The remaining heart tissues were stored at −80° C. FIG. 10 depicts a diagram of the rat surgical model and schematics of the experimental protocols.

Myocardial Injury Endpoints:

The following endpoints were assessed: plasma cTnI and heart-type fatty acid binding protein (HFABP, ELISA, Life Diagnosis); myocardial apoptosis as levels of cleaved caspase-3 (Western blot) and TUNEL assays (Roche); and echocardiographic left ventricular function. Myocardial levels of TNFα, IL-6, and myeloperoxidase (MPO) were analyzed by ELISA. SIRT3 and cytochrome c were measured in isolated mitochondria by Western blot.

Biochemical Analysis.

Blood samples were collected from each rat at 24 h after CPB/DHCA. Samples were immediately cooled to 4° C. and centrifuged at 3,000 rpm for 10 minutes at 4° C. Serum was collected and stored at −80° C. until assay. Whole cell lysate from heart tissues was obtained according to manufacturer's instruction (Panomics) and used for measurement of pro-inflammatory cytokines IL-6, TNFα and MPO by an ELISA method (Thermo Scientific). Cellular levels of ATP were measured by ELISA (Abeam).

Immunostaining and Confocal Microscopy.

Confocal studies were performed as described previously. Paraffin sections were deparaffinized using xylene and descending grades of ethanol, pretreated with microwave irradiation (350 W, for 5 min in 200 ml of 0.1M Citrate buffer, pH 6.0). Tissue sections were incubated with rabbit monoclonal IgG anti-SIRT3 (Cell Signaling) and mouse monoclonal IgG anti-COXIV (Cell Signaling) at 4° C. overnight. After washing, tissue sections were incubated with Alexa555 conjugated donkey anti-mouse IgG and Alexa488 conjugated goat anti-rabbit IgG (Molecular Probes) for 1 h at RT. Images were acquired with a confocal microscope (Zeiss Invert 510 Microscope). The control experiments were performed using mouse IgG and/or rabbit IgG.

Terminal Deoxynucleotidyl Nick-End Labeling (TUNEL).

TUNEL assay was performed using the In Situ Cell Death Detection Kit (Roche Molecular Biochemicals) according to manufacturer's protocol. Briefly, paraffin sections of heart tissue were deparaffinized as described above. Tissue sections were incubated with terminal deoxynucleotidyl transferase (TdT) enzyme for 1.5 h at 37° C. in order to bind to exposed 3'-OH ends of DNA fragments generated in response to apoptotic signals. The reaction was terminated with stop solution and fluorescent apoptotic signal was detected using a fluorescence microscope (Zeiss LSM 510 inverted confocal). Ten fields of each tissue section were randomly chosen and a total of 50 cells per field were counted. The index of apoptosis was determined (TUNEL positive myocytes/total myocytes counted×100%) from a total of 20 fields per heart, and the assays were performed in a blinded manner.

Statistical Analyses.

In all studies involving comparisons of more than two conditions, data were analyzed using an (ANOVA) F-test, and all other studies involving comparisons between two groups, data were analyzed using the Student's t-test. All results were represented as the mean±SD. Differences were considered significant when $P<0.05$.

ANXA1sp Displays Robust Cardioprotective Efficacy In Vivo in a Clinically Relevant Rat Experimental Models of Myocardial Ischemia-Reperfusion with Cardioplegic Arrest.

Figure 16:
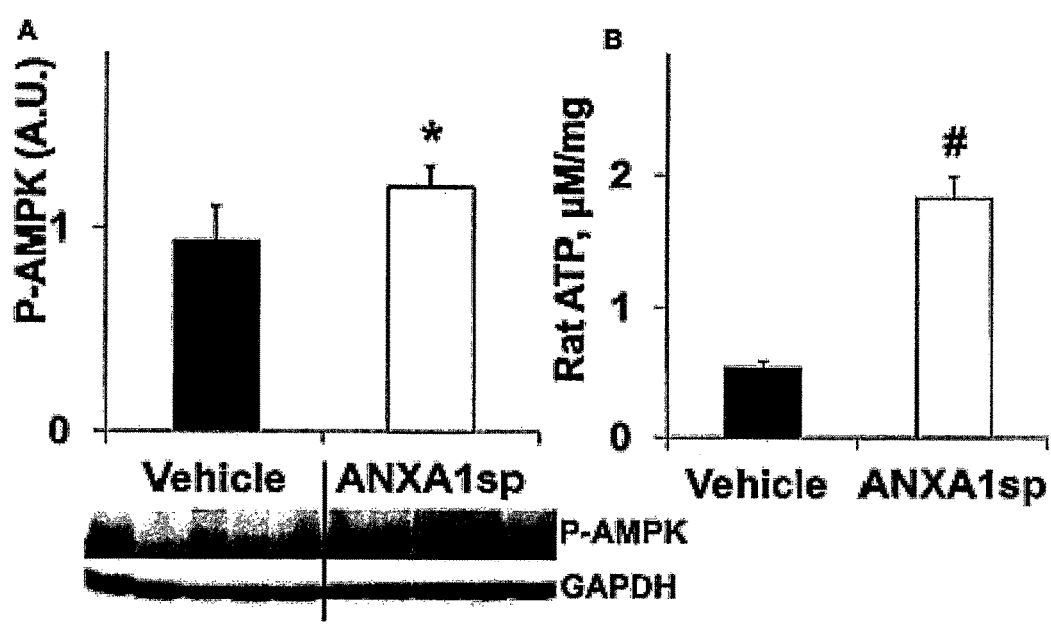
FIG. 16. Increased SIRT3 activity with ANXA1sp treatment is also associated with increased phosphorylation of AMP-activated protein kinase (P-AMPK) in left ventricular myocardial lysates from rats following 60 min DHCA and 3 h reperfusion (panel A, Western blot). This is correlated with increased myocardial levels of ATP in ANXA1sp treated animals (panel B). Results presented as mean±SD (n=5), *P<0.05 and #P<0.01. P-AMPK, phosphorylated AMPK. GAPDH used as loading control.

Rat findings: ANXA1sp (3 mg/kg)—administered in three doses 1 h prior to the onset of CPB, with cardioplegia, and at the completion of CPB—significantly reduced plasma biomarkers of myonecrosis (TnI, HFABP, FIGS. 11A,B) at multiple reperfusion time points (3, 6, 24 h), myocardial apoptosis, as evidenced by lower myocardial levels of activated caspase-3 (FIG. 11C) and TUNEL positive nuclei (FIG. 11D), myocardial leukocyte extravasation (MPO, FIG. 11E), and improved recovery of LV systolic function at 24 h post-reperfusion (LV-FAC 75±6% vs. 63±5% in ANXA1sp vs. vehicle treated controls, respectively P=0.02). Administration of scrambled peptide did not afford cardioprotection in the rat (FIGS. 11D, 11F). Because of the known effects of hyperglycemia to blunt cardioprotective mechanisms, the effects of ANXA1sp were further tested in rats rendered acutely hyperglycemic (blood glucose>300 mg/dl) through perioperative administration of Dextrose (25%, 5 gm/kg). In these animals, ANXA1sp also significantly attenuated the hyperglycemic exacerbation of myocardial injury and inflammation following cardioplegic arrest. Physiological parameters during the conduct of CPB/CA were similar between treatment groups. Finally, ANXA1sp improved myocardial energetics as evidenced by significantly higher myocardial ATP levels (FIG. 16B).

Cardioprotective Efficacy of ANXA1sp in DHCA Rats.

ANXA1sp significantly attenuated perioperative myocardial injury (PMI), as evidenced by significantly decreased myocardial apoptosis by TUNEL staining (FIG. 12A), cleaved caspase-3 activity by Western blot, and serum levels of myonecrosis biomarkers (by ELISA) cTnI (FIG. 12B) following 60 min of DHCA in the rat.

ANXA1sp Robustly Up-Regulated SIRT3 in DHCA Rats.

The expression pattern of SIRT3 was characterized (by Western blot) in the heart tissue lysates from DHCA rats. Consistent with in vitro findings in cardiomyocytes, DHCA rats treated with vehicle demonstrated downregulated expression (light bar, 44-kDa protein) and reduced activation (dark bar, 28-kDa protein) of myocardial SIRT3 at 3 hours post-perfusion (FIG. 13A, Sham vs. Vehicle; $p<0.005$). ANXA1sp significantly restored expression and activation of SIRT3 (ANXA1sp vs. Vehicle; $p<0.05$). A scrambled peptide (scrPEP) had no such effects (FIG. 13A, ANXA1sp vs. scrPEP; $p<0.005$). Overall, these findings indicate that SIRT3 plays a protective role in surgical IR and can likely be manipulated pharmacologically (e.g. by ANXA1sp).

Figure 14:
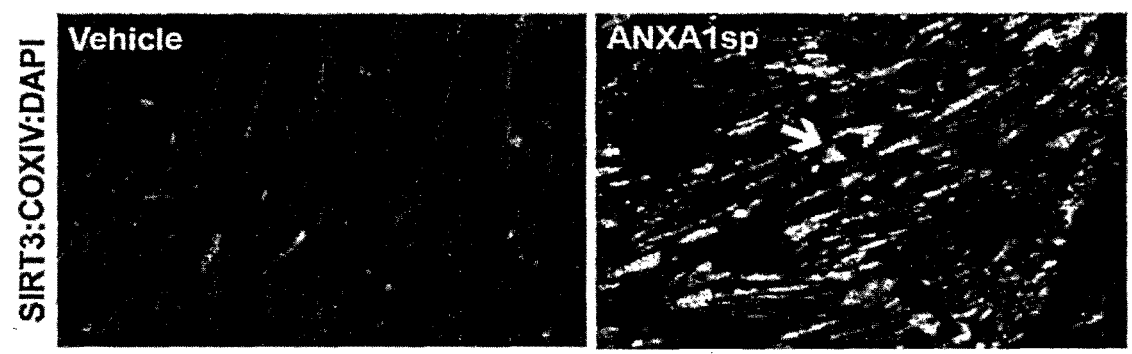
FIG. 14. In rats undergoing DHCA, ANXA1sp treatment increased expression of myocardial SIRT3. Activated SIRT3 predominantly localized in mitochondria (right panel, arrow). Animals underwent 60 min of DHCA at 18° C., followed by 3 h of reperfusion. SIRT3 (green), COXIV (mitochondrial marker, red), DAPI (nuclei, blue), and co-localization SIRT3-COXIV (yellow).

Consistent with in vitro findings in cultured cardiomyocytes, ANXA1sp treatment increased expression of mitochondrial SIRT3 in left ventricular myocardium from rats subjected to 60 min of DHCA. FIG. 14 depicts a confocal micrograph of a LV myocardial section, demonstrating colocalization of SIRT3 with the mitochondrial specific marker COX-IV.

In summary, using clinically relevant experimental models of cardiopulmonary bypass and cardioplegic arrest, we demonstrated that administration of ANXA1sp promotes cardiomyocyte survival and preserves contractile function following surgical IR in vitro and in vivo, by specifically upregulating expression and activity of mitochondrial SIRT3. Although not tested in animal models with comorbidity profiles similar to those of cardiac surgical patients, ANXA1sp was effective in the setting of acute hyperglycemia, known to interfere with the ability to protect ischemic myocardium. Furthermore, robust cytoprotective effects were also observed following hypoxia/reoxygenation in cultured adult cardiomyocytes, in the absence of inflammatory cells. This is the first report of a novel ANXA1-SIRT3 regulatory mechanism that is operational in the myocardium.

These preclinical findings facilitate the first human studies of ANXA1sp for reducing myocardial IR injury in patients undergoing cardiac surgery. These results indicate that, as a novel activator of SIRTs, this biologically active peptide (ANXA1sp) has the potential for perioperative/periprocedural cardioprotection. The research could be easily and feasibly expanded to study effects of ANXA1sp in neurological surgery, transplantation, and aging-related diseases such as cardiovascular diseases, cancer, and neurodegenerative disorders.

This technology provides a previously undescribed way of controlling myocardial inflammation, metabolism, cell survival/death, and ATP production without the significant side effects associated with currently available anti-inflammatory drugs and small molecule activators of SIRT1, and can be further facilitated by the recent development of synthetic, orally active non-peptide ANXA1 analogues. The focus on efficacy, using clinically relevant animal experimental models, and the novel mechanisms proposed are expected to overcome known barriers to clinical translation.

Example 2. Annexin A1 Regulation of Sirtuins

Myocardial ischemia-reperfusion (IR) injury remains a major cause of cardiovascular morbidity and mortality following cardiac surgery and transplantation. Mitochondrial dysfunction and myocardial inflammation play critical roles in mediating apoptosis and necrosis following myocardial IR. Annexin-A1 (ANXA1) has been implicated in cardioprotection through resolution of inflammation, and shown to regulate histone deacetylases. However, it is not yet known whether ANXA1 regulates sirtuins (SIRTs), $NAD^+$-dependent protein deacetylases and ADP-ribosyltransferases, following myocardial IR.

Seven members of the SIRT family have been identified in mammals. All share the same highly conserved $NAD^+$-binding site and a Sir2 catalytic core domain with variable amino and carboxyl residues. SIRT1-3 and SIRT5-7 catalyze $NAD^+$-dependent substrate-specific protein deacetylation, whereas SIRT4 acts as a $NAD^+$-dependent mono-ADP-ribosyltransferase. SIRT6 has both deacetylase and auto-ADP-ribosyltransferase properties.

Among SIRTs, SIRT3 is unique because it is the only analogue that, with increased expression, has been correlated with extended lifespan and enhanced health span in humans. SIRT3 is localized predominantly in the mitochondrial matrix and is referred to as a mitochondrial stress sensor that can modulate the activity of several mitochondrial proteins involved in metabolism, oxidative stress, free fatty acid oxidation, and maintenance of cellular ATP levels. In the heart, SIRT3 has been found to block development of cardiac hypertrophy, and protect cardiomyocytes from oxidative stress-mediated cell death. In addition, SIRT3 has been reported to have tumor-suppressive characteristics and anti-aging properties.

SIRT1 has been implicated in the prevention of many age-related diseases such as cancer, Alzheimer's disease, and type-2 diabetes. At the cellular level, SIRT1 controls DNA repair and apoptosis, circadian clocks, inflammatory pathways, insulin secretion, and mitochondrial biogenesis. Thus, increased expression of SIRTs—especially SIRT1 and 3—by a small molecule activator, could be beneficial for patients with cardiovascular diseases developing acute coronary syndromes, following cardiac surgery and transplantation, as well as those with age-related diseases.

To complement prior experiments that assessed the cardioprotective effects of ANXA1sp following surgical IR injury in vitro and in vivo by upregulating expression and activity of sirtuins and downstream signaling pathways, the studies outlined below sought to characterize the regulatory mechanisms underlying the SIRT-activating effects of ANXA1sp in vivo and in adult cardiomyocyte models of simulated IR.

ANXA1sp Activates Mitochondrial SIRT3 by Increasing Mitochondrial Processing Peptidase (MPP) in Response to IR In Vitro and In Vivo.

Figure 4:
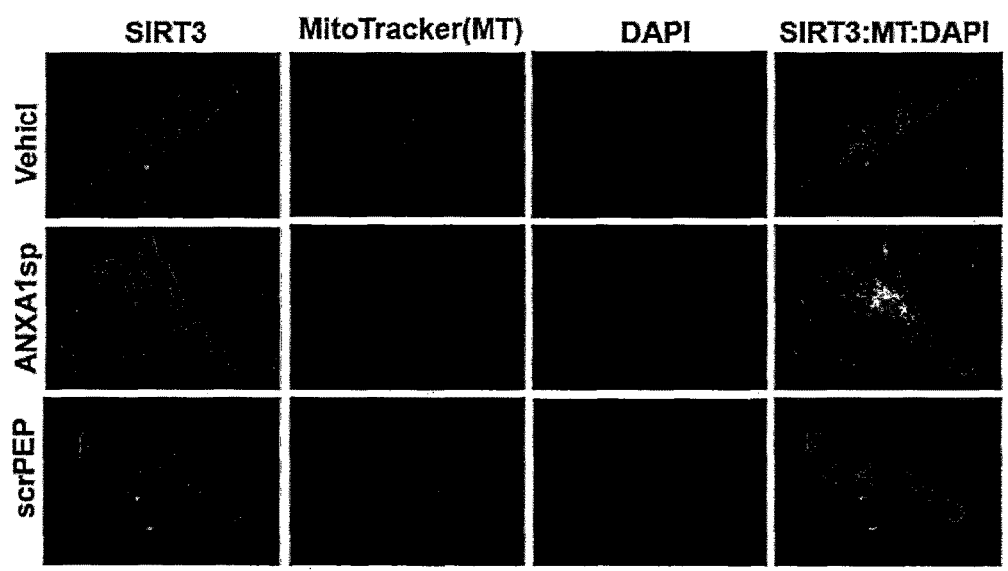
FIG. 4. ANXA1sp but not a scrambled peptide activates SIRT3 that predominantly localizes in mitochondria in cultured ARVCs. ARVCs were treated with 10 µM ANXA1sp or scrPEP for 1 h, subjected to 2 h OGD followed by 3 h reoxygenation. SIRT3 (green), MitoTracker (red), DAPI (nuclei, blue), co-localization SIRT3-MitoTracker (yellow).

Full-length human SIRT3 is a 44-kDa protein with an N-terminal mitochondrial localization sequence. Following import into the mitochondria, 142 amino acids from the N-terminal of full-length SIRT3 are cleaved by MPP to generate an active 28-kDa short form for the removal of the acetyl (Ac) group(s) from its target proteins. ANXA1sp but not scrPEP significantly increased MPP both in vitro, in cultured ARVCs subjected to OGD (FIG. 2, lower panel), as well as in vivo, in rat myocardium following DHCA (FIG. 13B). To define the expression/activation pattern of SIRT3 in response to surgical IR, SIRT3 was localized (cytoplasm, nucleus, or mitochondria) or precisely "tracked" using a combination of immunostaining and confocal microscopy to recognize SIRT3, mitochondrial marker Complex IV (COXIV), nucleus and the co-localization between SIRT3 and COXIV. It was found that, following surgical IR, ANXA1sp robustly increased SIRT3 and was predominantly localized in the mitochondria of rat myocardium (FIG. 14), where SIRT3 deacetylates and regulates mitochondrial proteins. Conversely, it was found that SIRT3 was located in the nucleus and cytoplasm in rats treated with vehicle. scrPEP has no such effects. These findings were replicated in vitro, in ARVCs subjected to OGD/reoxygenation (FIG. 4).

Figure 5:
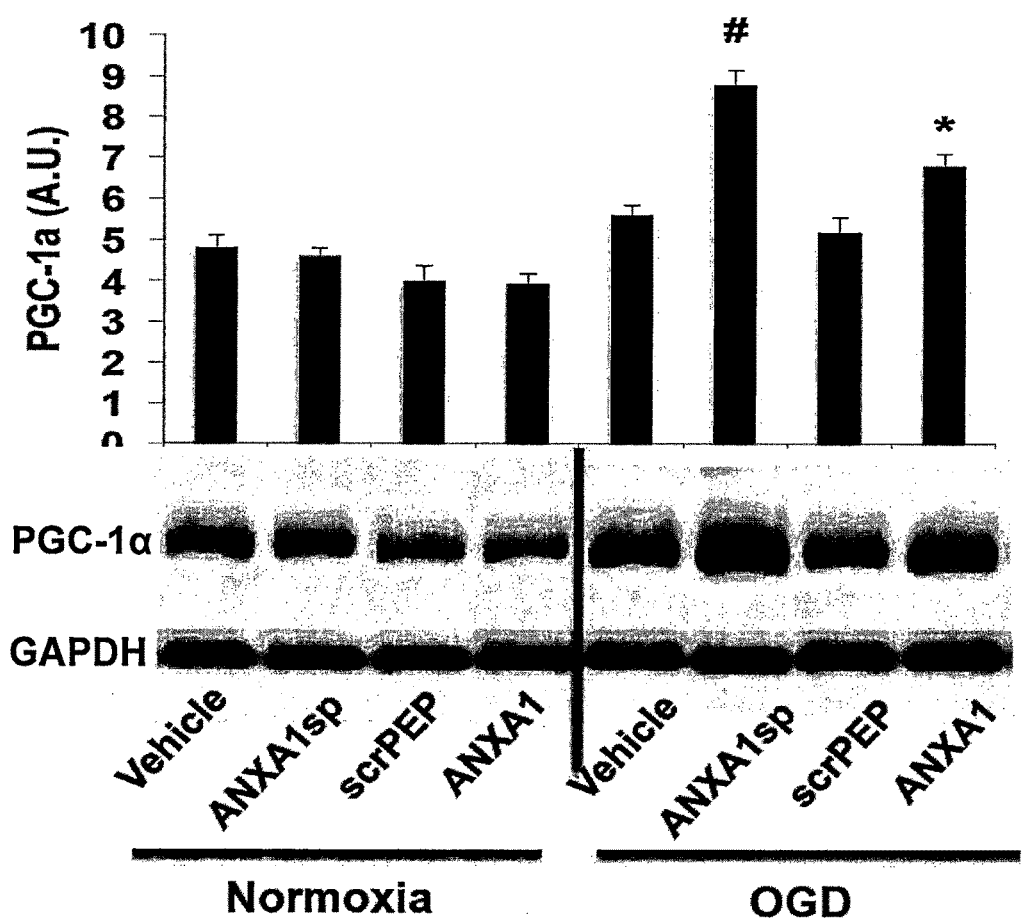
FIG. 5. ANXA1sp but not a scrambled peptide increased cellular expression of PGC1-α in ARVCs subjected to 2 h OGD followed by 3 h reoxygenation. scrPEP, scrambled peptide; A1, Annexin A1 full-length protein. GAPDH used as loading control.

In addition to the upregulation of mitochondrial processing peptidase implicated in regulating mitochondrial activation of SIRT3, treatment with ANXA1sp was also associated with upregulation of Peroxisome proliferator-activated receptor-gamma coactivator (PGC)-1alpha, is a member of a family of transcription coactivators that plays a central role in the regulation of cellular energy metabolism and known regulator of SIRT3 expression (FIG. 5).

ANXA1sp Activates Other Members of the Sirtuin Family.

Figure 17:
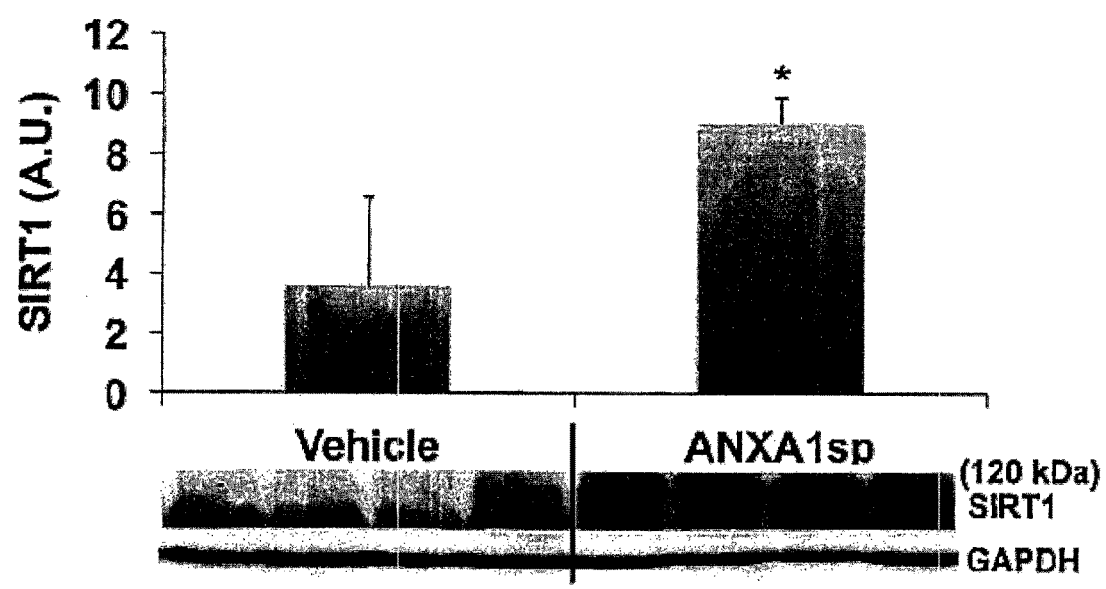
FIG. 17. ANXA1sp increases myocardial levels or SIRT1 following DHCA in rats. Rats underwent 60 min DHCA at 18° C. and received either vehicle or ANXA1sp (2 mg/kg, iv) followed by 6 hours reperfusion. Expression of SIRT1 was determined in left ventricular myocardium tissue lysates by Western blot. Results presented as mean±SD (n=4), *p<0.01. DHCA, deep hypothermic circulatory arrest. GAPDH used as loading control.
Figure 18:
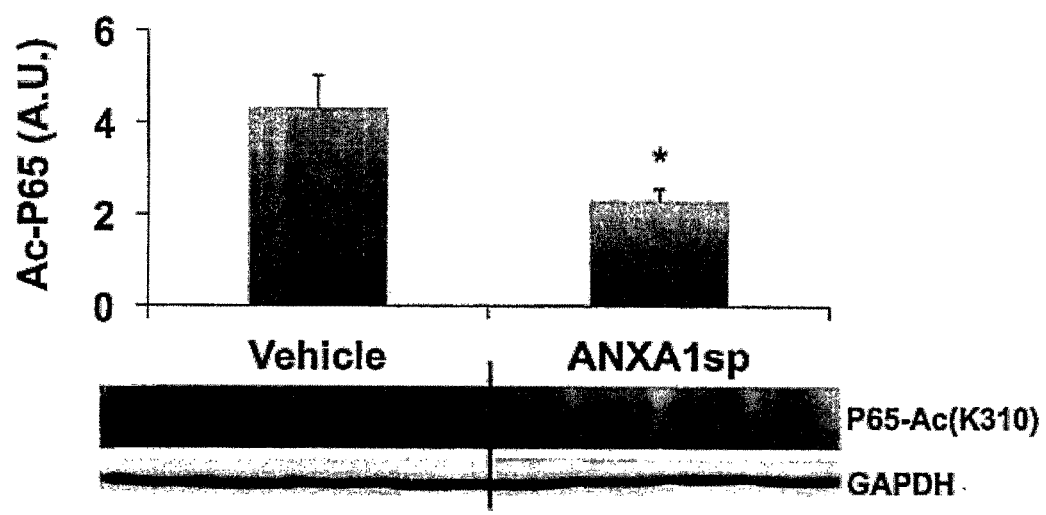
FIG. 18. Increased SIRT1 expression with ANXA1sp treatment is also associated with reduced acetylation of NF-κB p65 subunit (at lysine 310 residue) following DHCA in rats. Rats underwent 1 hour DHCA at 18° C. and received either vehicle or ANXA1sp (2 mg/kg, iv) followed by 6 hours reperfusion. Levels of acetylated NF-κB p65 were determined in left ventricular myocardium tissue lysates by Western blot. Results presented as mean±SD (n=4), *p<0.001. DHCA, deep hypothermic circulatory arrest; P65-Ac(K310), lysine 310 acetylated NF-κB p65 subunit. GAPDH used as loading control.

Moreover, we found in DHCA rats, that administration of ANXA1sp robustly increased cellular expression of SIRT1 as well (FIG. 17), attenuated acetylation of NF-kB p65 (K310, FIG. 18), and suppressed NF-κB transcriptional activity, as evidenced by significantly down-regulated NF-κB-mediated gene expression of TNFα.

Example 3. Sirtuin-3 Modulation of Acetylation in the Treatment of Perioperative Myocardial Reperfusion Injury Emerging evidence suggests that a novel post-translational lysine deacetylation has recently emerged as an important regulator for gene expressions as well as enzyme activities that involved in various biological functions including the function of mitochondria. Sirtuins (SIRTs), $NAD^+$-dependent protein deacetylases, mediate this post-translational modification by removing the acetyl groups from a wide range of proteins that have recently been demonstrated to be important in variety of diseases. Among 7 mammalian SIRTs, SIRT3 is the only analogue whose increased expression has been correlated with extended lifespan and enhanced health span in humans as well as implicated in variety of diseases. However, it remains unknown of whether SIRT3 can protect the heart from ischemia-reperfusion (IR) injury following cardiac surgery. We have recently found that a novel cardioprotective agent Annexin-A1 tripeptide (ANXA1sp) protects the heart from IR injury via increased SIRT3. Further, new preliminary data indicates that ANXA1sp-induced SIRT3 promotes survival of cultured rat adult cardiomyocytes after oxygen-glucose deprivation (OGD). We hypothesize that increased SIRT3 protects the heart form IR injury following cardiac surgery via lysine deacetylation of mitochondrial proteins involved in fuel oxidation, ATP production, antioxidant defenses, and cell survival. Currently, the treatment for perioperative myocardial injury (PMI) is limited and identifying agents to prevent/treat PMI has proved to be difficult. Therefore, it would be of tremendous benefit to identify and characterize the protective effect of SIR3 in order to identify small molecule modulators and drug design for treatment intervention.

Perioperative myocardial injury (PMI) due to ischemia-reperfusion (IR) remains a major cause of cardiovascular morbidity and mortality. Sirtuin-3 (SIRT3), one of 7 mammalian protein deacetylases, is an attractive target for small molecule activators, and plays a key role in treating a variety of diseases and in extending lifespan. SIRT3 has received attention for its role in catalyzing lysine residue deacetylation of mitochondrial proteins involved in fuel oxidation, energy production, oxidative stress responses, and cell survival. Mice lacking SIRT3 have hyperacetylated mitochondrial proteins, defects in fatty acid oxidation, reduction in ATP production, and induced oxidative stress.

These studies were designed to determine whether pharmacologically increasing SIRT3 protects the heart form surgical IR injury via enhancing lysine deacetylation of mitochondrial proteins. The rationale for using ANXA1sp as a modulator of SIRT3 activity in the heart stems from the following findings: 1) myocardial levels of SIRT3 are reduced in rats following deep hypothermic circulatory arrest (DHCA); 2) in DHCA rats, a small molecule SIRT activator (Annexin-A1 tripeptide; ANXA1sp) significantly increases expression and activation of SIRT3 that up-regulates manganese-containing superoxide dismutase (Mn-SOD) thereby attenuating reactive oxygen species (ROS), increases AMP-activated protein kinase (AMPK) for ATP production, and enhances myocardial tolerance to surgical IR; 3) ANXA1sp promotes survival of cultured rat adult ventricular cardiomyocytes (ARVCs) after oxygen-glucose deprivation (OGD) via increased SIRT3. Regulation of SIRT3 expression/activation in the heart subject to cardiac surgical stress, through post-translational lysine deacetylation (↑ATP, ↓ROS, ↑cell survival) can likely be manipulated pharmacologically, resulting in new and innovative approaches to prevent and/or treat PMI due to IR and IR-related diseases such as ischemic heart diseases.

Each year, more than 260,000 cardiac surgical procedures are performed in the US, with associated health care costs totaling approximately $503.2 billion dollars. Despite advances in surgical, anesthetic, and cardioprotective strategies, the incidence of perioperative myocardial injury (PMI) due to ischemia-reperfusion (IR) remains at 7-19%, and is consistently associated with increased perioperative morbidity and reduced short- and long-term survival. Identifying agents to prevent/treat PMI has proved to be difficult. The major translational barriers at the preclinical level include inappropriate animal models, lack of emphasis on efficacy, and imprecisely defined mechanisms. Thus, identifying new therapeutic targets and developing novel, effective, and safe agents to prevent and/or treat PMI represent an unmet clinical need and first priority for research and health care.

These studies were designed to identify a role of SIRT3 in a setting of surgical IR to allow for an understanding of how to manipulate SIRT3-mediated post-translational lysine deacetylation for perioperative cardioprotection: increased SIRT3→post-translational lysine deacetylation→cell survival. These studies will potentially lead to the development of pharmacologic strategies that will allow the targeting a number of cardioprotective mitochondrial proteins known to be regulated via SIRT3-mediated post-translational lysine deacetylation. Once such strategies are developed, PMI and IR-related diseases are likely be prevented and/or treated via manipulating post-translational lysine deacetylation. Pharmacologically increasing SIRT3 activity, alone, is likely to be sufficient for this purpose. It is also expected that these technologies can be equally applicable to perioperative neuroprotection and renal protection after cardiac surgery as well as age-related diseases.

Although the potential importance of acetyl-modification of protein lysine residues has been recognized for several decades, the appreciation that this post-translational modification is highly prevalent in mitochondria and plays pivotal a regulatory role in mitochondrial function has only recently become apparent. Although post-translational lysine deacetylation mediated by SIRTs has been noted in a variety human diseases and lifespan, it still remains unknown what the role of SIRTs is in surgical IR. To the inventors' knowledge, no small molecule SIRT3 activators have yet been identified. As described in the present invention, a small molecule, ANXA1sp, robustly increases SIRT3 and protects the heart form surgical IR injury. These studies indicate that SIRT3-mediated post-translational lysine deacetylation in the heart undergoing cardiac surgery can likely be manipulated pharmacologically. This approach is expected to identify new therapeutic targets, and provide fundamental knowledge for mechanism-based drug development, which would eventually lead to an efficacious cardioprotective strategy in a setting surgical IR.

Myocardial IR injury is associated with metabolic alterations including the generation of reactive oxygen species (ROS), ATP depletion, and cell death. Mitochondria serve as important end targets, mediating cell death resulting from myocardial IR. Therefore, the mitochondrion is a critical determinant of lethal reperfusion injury, and as such, it is an important new target for cardioprotection. Full-length human SIRT3 is a 44-kDa protein with an N-terminal mitochondrial localization sequence. Following import into the mitochondria, 142 amino acids from the N-terminal of full-length SIRT3 are cleaved by mitochondrial processing peptidase (MPP) to generate an active 28-kDa short form for the removal of the acetyl (Ac) group(s) from its target proteins. Mice lacking SIRT3 have hyperacetylated mitochondrial proteins, a primary defect in fatty acid oxidation, ATP reduction, and induced oxidative stress, suggesting that SIRT3 is a major mitochondrial deacetylase. Thus, precisely manipulating SIRT3 can likely be sufficient to maintain mitochondrial homeostasis, enhance cell survival, and reduce surgical IR injury.

Figure 11:
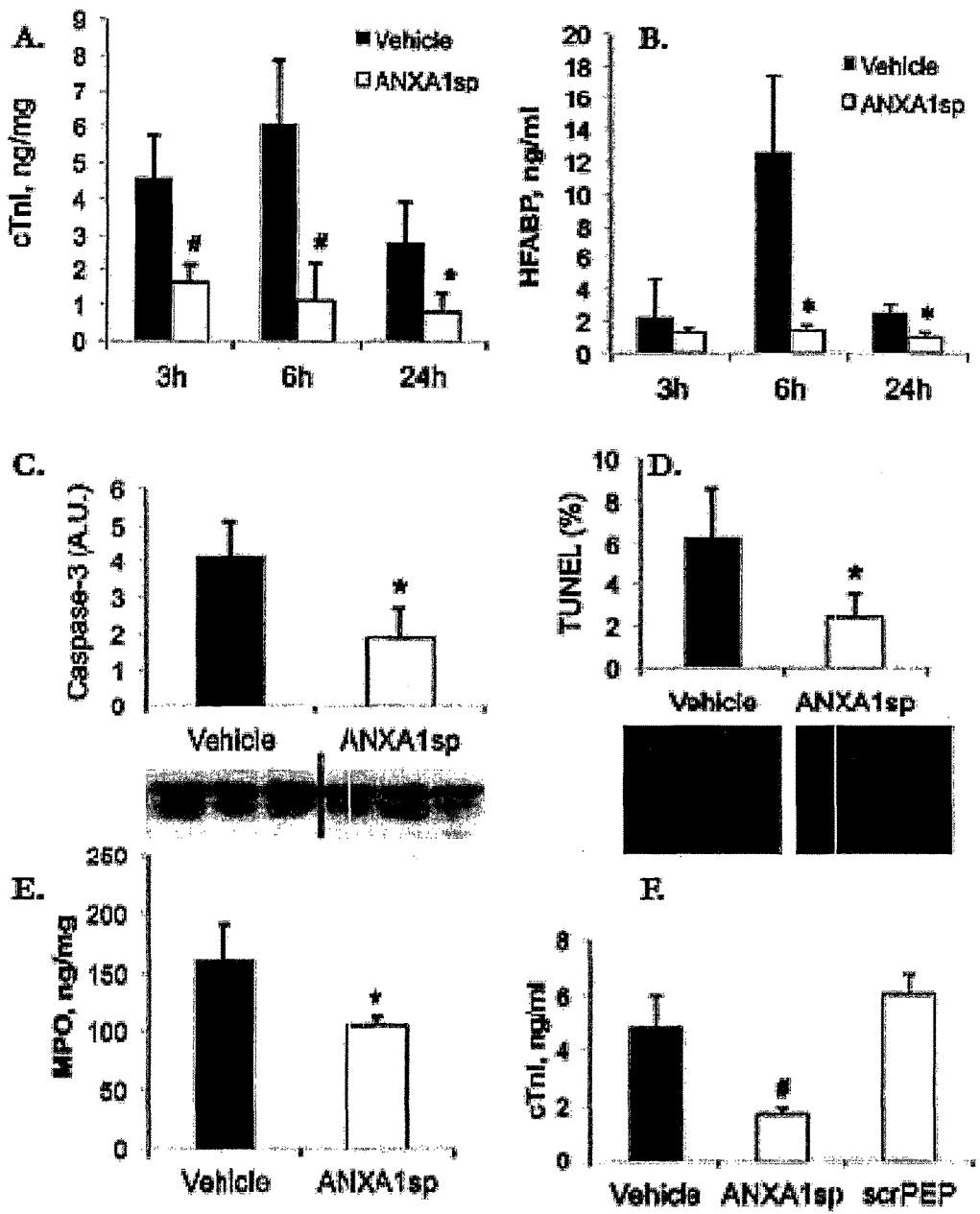
FIG. 11. Cardioprotective efficacy of ANXA1sp compared to vehicle control following 45 min of cardioplegic arrest, assessed at different reperfusion time points using conventional biomarkers of myonecrosis (plasma Troponin I and heart fatty-acid binding protein using rat-specific ELISA, Life Diagnostics), apoptosis (cleaved caspase-3 by Western blot and TUNEL staining of LV sections), and myocardial levels of myeloperoxidase (MPO, analyzed by ELISA). Administration of ANXA1sp (3 mg/kg) reduces plasma levels of myocardial injury biomarkers at multiple reperfusion time points (A, B), attenuates myocardial apoptosis (C, D, reperfusion 24 h), and leukocyte extravasation (MPO) into the myocardium (E), when compared to vehicle treated control or to scrambled peptide (F, reperfusion 3 h). cTnI, cardiac troponin I; HFABP, heart-type fatty acid binding protein; MPO, myeloperoxidase; scrPEP, scrambled peptide. Data presented as mean±SD. *P<0.05 and #P<0.01 versus vehicle treated control (n=8/group).
Figure 12:
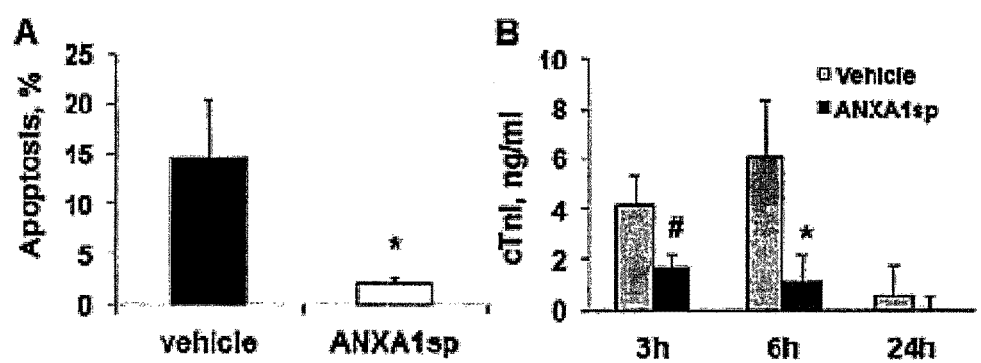
FIG. 12. Cardioprotective efficacy of ANXA1sp compared to vehicle control following 60 min of deep hypothermic cardioplegic arrest, assessed at different reperfusion time points using conventional biomarkers of myonecrosis (plasma Troponin I, rat-specific ELISA, Life Diagnostics), apoptosis (TUNEL staining of LV sections at 24 h post-reperfusion). Administration of ANXA1sp (3 mg/kg) reduces plasma levels of cTnI at multiple reperfusion time points (B) and attenuates myocardial apoptosis (A, reperfusion 24 h), when compared to vehicle treated control animals. cTnI, cardiac troponin I. Data presented as mean±SD. #P<0.05 and *P<0.001 versus vehicle treated control (n=8/group).
Figure 13:
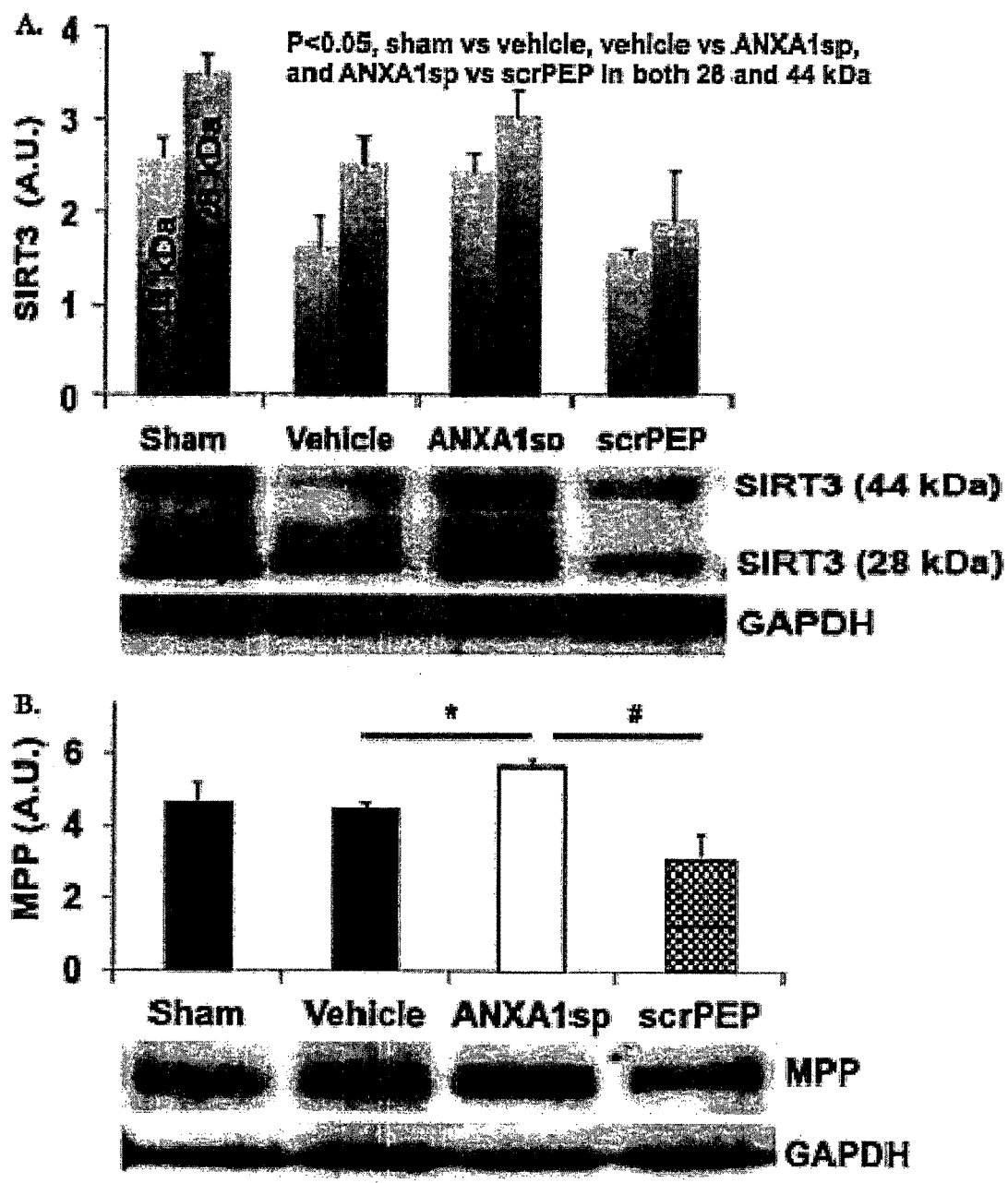
FIG. 13. ANXA1sp but not scrambled peptide (scrPEP) increases expression of SIRT3 (both 44-kD and 28-kD isoforms) in left ventricular myocardium from rats following deep hypothermic circulatory arrest (DHCA, panel A). This was associated with increased myocardial expression of mitochondrial matrix processing peptidase (MPP, panel B). Rats underwent 60 min of DHCA at 18° C., and received either vehicle, scrambled peptide, or ANXA1sp (2 mg/kg, iv), followed by 3 h of reperfusion. Sham animals served as baseline control. SIRT3 was determined in tissue lysates by Western blot. SIRT3 44-kD isoform, light bars; SIRT3 28-kD isoform, dark bars. Results presented as mean±SD (n=5/group), *P<0.05, #P<0.01. GAPDH used as loading control.

Studies were conducted to determine whether increased SIRT3 protects the heart from IR injury following cardiac surgery. To test this, the expression pattern of SIRT3 was characterized (by Western blot) in experimental models of surgical IR. DHCA rats treated with vehicle demonstrated suppressed expression (44-kDa protein) and reduced activation (28-kDa protein) of myocardial SIRT3 at 3 hours post-perfusion (FIG. 13A, sham vs. vehicle; p<0.005). A novel cardioprotective agent ANXA1sp exhibited cardioprotective efficacy with robustly increased expression and activation of SIRT3 (FIG. 13A, ANXA1sp vs. vehicle; p<0.05) and this associated with ANXA1sp-mediated perioperative cardioprotection (FIGS. 11, 12). Interestingly, a scrambled peptide (scrPEP) had no such effects (FIG. 13, ANXA1sp vs. scrPEP; p<0.005). These findings indicate that SIRT3 plays a protective role in surgical IR and can likely be manipulated pharmacologically (e.g., by ANXA1sp).

To define the expression/activation pattern of SIRT3 in response to surgical IR, SIRT3 was localized (cytoplasm, nucleus, or mitochondria) or precisely "tracked" by using a combination of immunostaining and confocal microscopy. Following surgical IR, ANXA1sp robustly increased SIRT3 in both full-length (44-kDA) and short active form (28-kDa) SIRT3 proteins and it predominantly located in the mitochondria of rat myocardium, where it deacetylates and regulates mitochondrial proteins. In addition, SIRT3 was found in both the nucleus and cytoplasm in rats treated with vehicle (FIG. 14).

ANXA1sp Increased/Activated SIRT3 that Regulated its Target Proteins in DHCA Rats.

Figure 15:
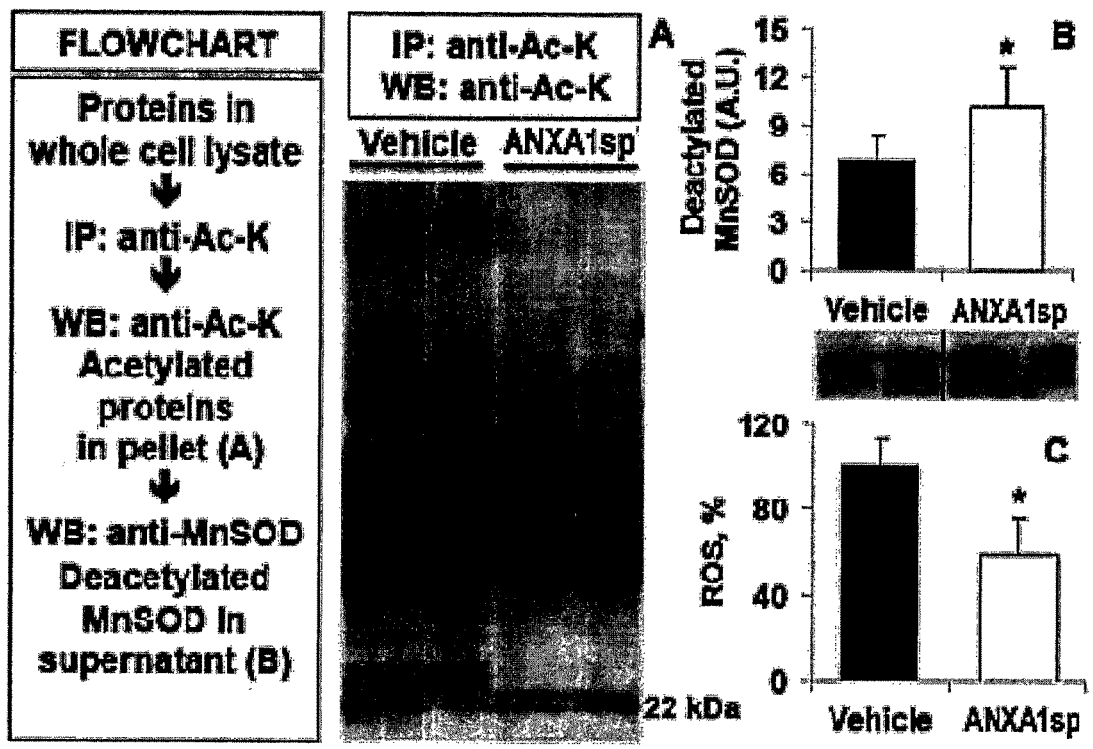
FIG. 15. Increased SIRT3 activity with ANXA1sp treatment is associated with reduced protein lysine acetylation in left ventricular myocardial lysates from rats following 60 min DHCA and 6 h reperfusion (panel A). This included deacetylation of MnSOD (known to increase its reactive oxygen species scavenging activity). Acetylated proteins were immunoprecipitated with anti-acetyl lysine antibody, and deacetylated MnSOD levels were assessed in the supernatant via Western blot (panel B). This is accompanied by decreased cellular levels of reactive oxygen species in ANXA1sp treated hearts (panel C, ELISA). Results presented as mean±SD (n=5/group), *P<0.05. anti-Ac-K, acetylated lysine antibody; IP, immuno-precipitation; WB, Western blot; ROS, reactive oxygen species; MnSOD, manganese superoxide dismutase.

In DHCA rats, it was found that ANXA1sp significantly increased: 1) expression and activation of SIRT3 that up-regulates manganese-containing superoxide dismutase (MnSOD) for attenuating reactive oxygen species (ROS) (FIGS. 15B, C), AMP-activated protein kinase (AMPK) for ATP production (FIGS. 16A, B), and eventually enhances myocardial tolerance to surgical IR, as evidenced by reduced myocardial apoptosis and necrosis (see FIG. 12). Treatment with ANXA1sp resulted in significant reduction of protein acetylation in myocardial tissue homogenates (FIG. 15A), as well as an increase in the deacetylated (active form) of Manganese-Superoxide Dismutase (FIG. 15B).

ANXA1sp Increased/Activated SIRT3 that Regulated its Down-Stream Target Proteins In Vitro.

Figure 6:
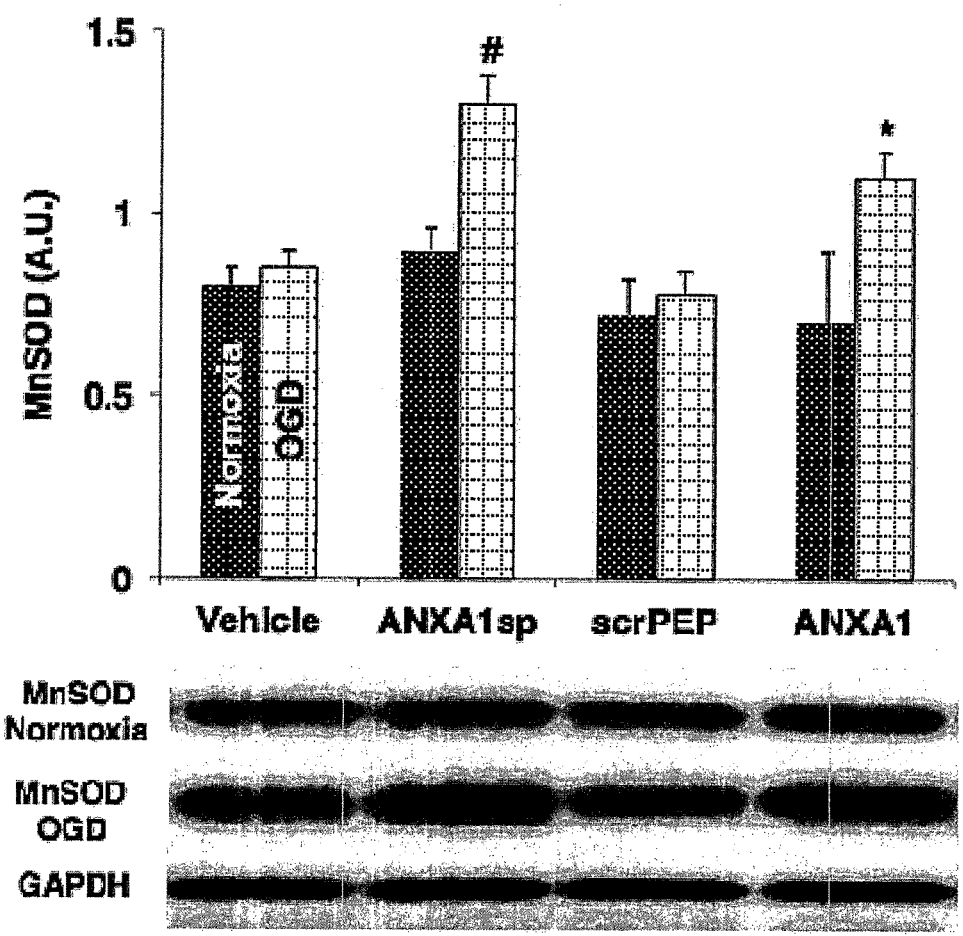
FIG. 6. Increased SIRT3 activity with ANXA1sp treatment is associated with increased expression of antioxidant enzyme manganese-superoxide dismutase (MnSOD, known to be regulated by SIRT3) in adult rat ventricular cardiomyocytes subject to 2 h OGD and 3 h reoxygenation. Results presented as mean±SD (n=3), *$P<0.05$ and #$P<0.01$. scrPEP, scrambled peptide; ANXA1, Annexin A1 full-length protein; OGD, oxygen-glucose deprivation. GAPDH used as loading control.
Figure 7:
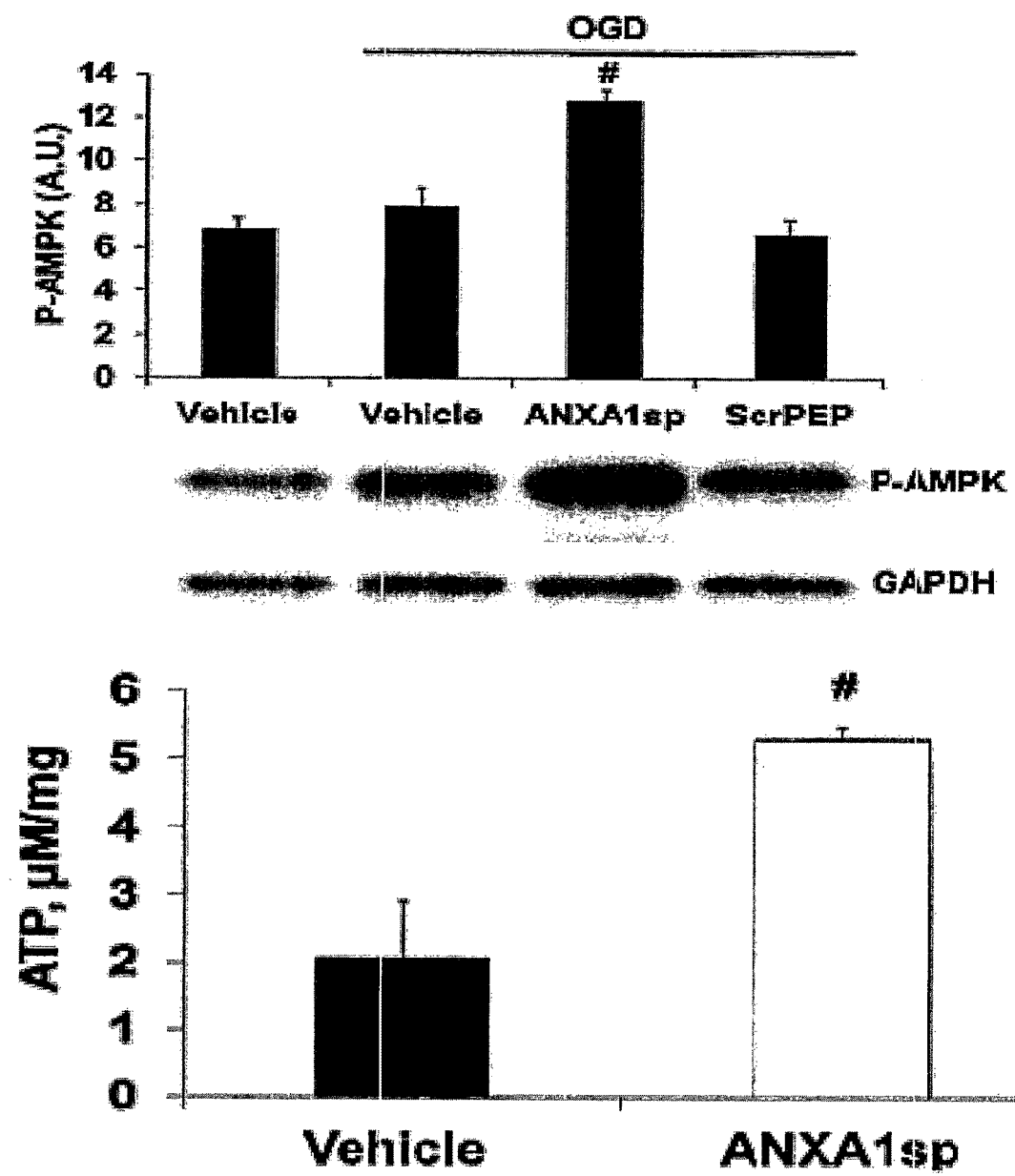
FIG. 7. Increased SIRT3 activity with ANXA1sp treatment is also associated with increased phosphorylation of AMP-activated protein kinase (P-AMPK) in adult rat ventricular cardiomyocytes subject to 2 h OGD and 3 h reoxygenation. Phosphorylation of AMPK is known to occur indirectly via SIRT3 activation of serine-threonine liver kinase B1 (LKB1), which subsequently phosphorylates and activates AMPK, with many downstream cardioprotective targets (panel A). This is correlated with increased cellular levels of ATP in ANXA1sp treated cardiomyocytes (panel B). Results presented as mean±SD (n=3), #$P<0.01$. scrPEP, scrambled peptide; OGD, oxygen-glucose deprivation; P-AMPK, phosphorylated AMPK. GAPDH used as loading control.
Figure 9:
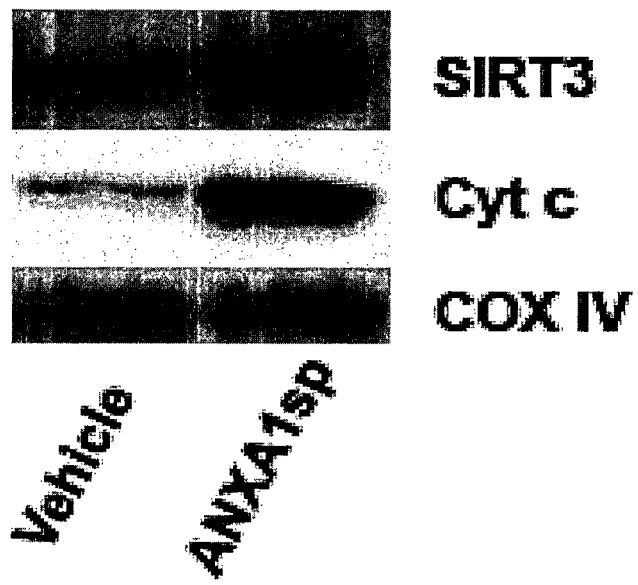
FIG. 9. ANXA1sp enhanced mitochondrial dynamic function in the setting of simulated IR. ARVCs treated with ANXA1sp showed higher levels of mitochondrial cytochrome c (cyt c) and sirtuin 3 (SIRT3) following 2 h OGD and 3 hours reoxygenation. COX-IV used as loading control.

These findings were confirmed in vitro, in cultured adult rat ventricular cardiomyocytes. ANXA1sp treatment results in significant reduction in protein acetylation following OGD/reoxygenation (FIG. 3B). This is further associated with increased expression of total MnSOD (FIG. 6), increased phosphorylation of AMPK (FIG. 7, upper panel) and increased ATP concentrations (FIG. 7, lower panel) in ARVCs. Importantly, this correlated with maintained mitochondrial cytochrome c expression (FIG. 9), and ultimately enhanced ARVCs tolerance to simulated IR, as evidenced by reduced cell apoptosis and necrosis (FIG. 1).

Figure 8:
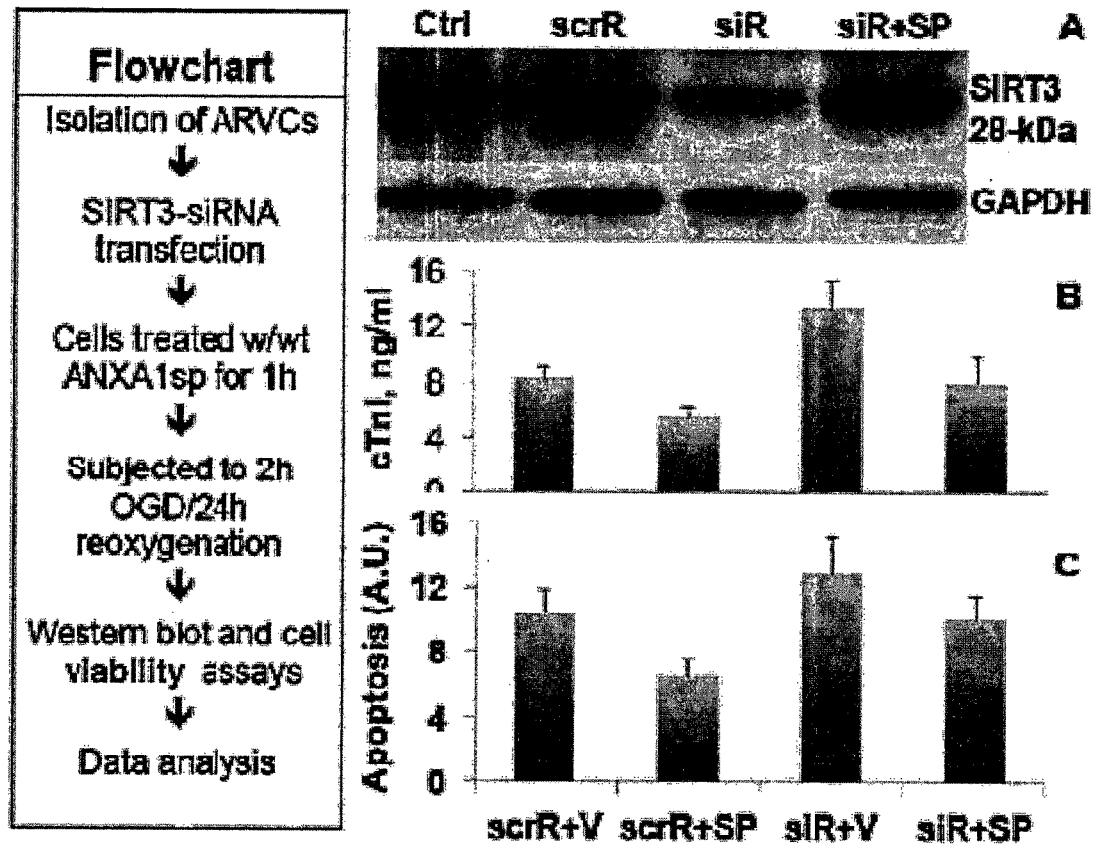
FIG. 8. siRNA-mediated knock-down of SIRT3 expression in adult ventricular cardiomyocytes (panel A) results in increased cell necrosis (panel B) and apoptosis (panel C) following simulated ischemia-reperfusion, which are partially rescued by ANXA1sp treatment (panels A-C). ARVC siRNA transfection: after 24 h of incubation with AW Medium (Cellutron Cat #M-8034) without antibiotics, ARVCs were transfected with a specific SIRT3-siRNA or a scrambled RNA (scrRNA) as control, according to manufacturer's protocol (Santa Cruz). Transfection efficiency was estimated by Western blotting of the target protein (A). ARVC, adult rat ventricular cardiomyocytes; OGD, oxygen-glucose deprivation; scrR, scrambled RNA; siR, SIRT3 siRNA; SP, ANXA1sp; V, vehicle control; scrR+V, scramble RNA with vehicle control; scrR+SP, scramble RNA with ANXA1sp; siR+V, SIRT3 siRNA with vehicle control; siR+SP, SIRT3 siRNA with ANXA1sp; cTnI, cardiac troponin I measured in supernatant. Results presented as mean±SD (n=3). GAPDH used as loading control.

Loss-of-function experiments using siRNA-mediated knock down of SIRT3 in cardiomyocytes resulted in increased cell necrosis and apoptosis, which were partially rescued by treatment with ANXA1sp but not with a scrambled peptide (FIG. 8).

The studies described herein show that SIRT3 expression and acetylation status of its target proteins can be manipulated pharmacologically (e.g., by ANXA1sp) in a rat model of DHCA, and reveal regulatory mechanisms of SIRT3-mediated post-translational lysine deacetylation in attenuating PMI in clinically relevant experimental models of surgical IR. Further studies will include determining whether SIRT3, or other 6 SIRTs, affects 1) cell receptors, such as G protein-coupled receptor formyl peptide receptor2 (FPR2), glucocorticoid receptor (GR), and toll-like receptor (TLR) such as TLR4, which is involved in global myocardial I/R injury; 2) mitochondria permeability and integrity; 3) calcium signaling; and 4) oxidative stress.

Furthermore, studies will be designed to investigate IR injury in other organs, including the brain and kidney after cardiac surgery, and to investigate other conditions with a known age-related pathogenesis, such as cardiovascular diseases, neuron degeneration disease, cancer, diabetes, metabolic syndrome, etc.

Using clinically relevant models of global myocardial ischemia-reperfusion model by cold cardioplegic arrest and cardiopulmonary bypass (resulting in further inflammatory activation and phenotypic priming of leukocytes) as opposed to models of local warm myocardial ischemia-reperfusion injury by coronary ligation, coupled to the emphasis on efficacy endpoints in multiple species and the clearly defined novel mechanism of action strengthen the relevance of this study to intraoperative cardioprotection, and should enable more rapid translation of these findings to first-in-man trials. Several advantages of short peptide therapeutics in perioperative cardioprotection include high target specificity and affinity, ability to be synthesized rather than expressed, better tissue penetration and non-immunogenicity, and compatibility with cold cardioplegia solutions without any stability issues.

The foregoing examples are illustrative of the present invention, and are not to be construed as limiting thereof. The invention is described by the following claims, with equivalents of the claims to be included therein.

All publications, patent applications, patents and other references cited herein are incorporated by reference in their entireties for the teachings relevant to the sentence and/or paragraph in which the reference is presented.

What is claimed is:

1. A method of increasing the amount and/or the activity of one or more than one sirtuin in a subject in need thereof, comprising administering to the subject an effective amount of ANXA1 short peptide (ANXA1sp), wherein the subject has type 2 diabetes, a metabolic disorder, obesity, a fat-related metabolic disorder, a neurodegenerative disorder, a disorder resulting in cognitive decline, a spinal cord injury, a blood coagulation disorder, an ocular disorder, a respiratory disorder, a viral infection, a fungal infection, chronic hepatitis infection, an autoimmune disorder, flushing, a mitochondrial disease or disorder, a chemotherapy-induced neuropathy, a skin disorder, affliction or condition, a disorder associated with stress, stroke, arthritis, hypertension, Alzheimer's disease, liver disease, an inflammatory disorder, trauma and/or chronic pain associated with brain and/or spinal cord disease, disorder, damage or injury, and any combination thereof, and further comprising the step of administering one or more compounds selected from the group consisting of resveratrol, piceatannol, nicotinic acid, and any combination thereof, prior to, concurrent with and/or after administration of the ANXA1 short peptide.

2. The method of claim 1, wherein the one or more than one sirtuin is selected from the group consisting of Sirtuin 1 (SIRT1), Sirtuin 2 (SIRT2), Sirtuin 3 (SIRT3), Sirtuin 4 (SIRT4), Sirtuin 5 (SIRT5), Sirtuin 6 (SIRT6) Sirtuin 7 (SIRT7), and any combination thereof.

* * * * *

UNITED STATES PATENT AND TRADEMARK OFFICE
CERTIFICATE OF CORRECTION

PATENT NO. : 10,172,915 B2
APPLICATION NO. : 14/519000
DATED : January 8, 2019
INVENTOR(S) : Zhang et al.

Page 1 of 1

It is certified that error appears in the above-identified patent and that said Letters Patent is hereby corrected as shown below:

On the Title Page

Item (56) References Cited, OTHER PUBLICATIONS, Aravindan cite:
Please correct "Kappa Bi n" to read -- Kappa B in --

Item (56) References Cited, OTHER PUBLICATIONS, Bell cite:
Please add the following to the end of the citation: -- (2011) --

Item (56) References Cited, OTHER PUBLICATIONS, Cao cite:
Please correct "NF-kB" to read -- NF-κB --

Item (56) References Cited, OTHER PUBLICATIONS, Dirksen cite:
Please correct "irjury" to read -- injury --

Item (56) References Cited, OTHER PUBLICATIONS, Facto cite:
Please correct "Facto" to read -- Facio --

Item (56) References Cited, OTHER PUBLICATIONS, 4th Zhang cite:
Please correct "NF-kB" to read -- NF-κB --

Signed and Sealed this
Ninth Day of April, 2019

Andrei Iancu
*Director of the United States Patent and Trademark Office*